US009295713B2

(12) United States Patent
Smith et al.

(10) Patent No.: US 9,295,713 B2
(45) Date of Patent: Mar. 29, 2016

(54) TREATMENT OF CHRONIC NEPHROPATHIES USING SOLUBLE COMPLEMENT RECEPTOR TYPE I (SCR1)

(75) Inventors: Richard J. H. Smith, Iowa City, IA (US); Yuzhou Zhang, Coralville, IA (US); Henry C. Marsh, Reading, MA (US)

(73) Assignees: CELLDEX THERAPEUTICS, INC., Needham, MA (US); UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 639 days.

(21) Appl. No.: 13/233,916

(22) Filed: Sep. 15, 2011

(65) Prior Publication Data

US 2012/0071413 A1 Mar. 22, 2012

Related U.S. Application Data

(60) Provisional application No. 61/383,004, filed on Sep. 15, 2010.

(51) Int. Cl.
*A61K 38/00* (2006.01)
*A61P 13/12* (2006.01)
*A61K 38/17* (2006.01)

(52) U.S. Cl.
CPC .................................. *A61K 38/1725* (2013.01)

(58) Field of Classification Search
None
See application file for complete search history.

(56) References Cited

U.S. PATENT DOCUMENTS

| | | | |
|---|---|---|---|
| 5,252,216 | A | 10/1993 | Folena-Wasserman et al. |
| 5,456,909 | A | 10/1995 | Marsh et al. |
| 5,840,858 | A | 11/1998 | Smith et al. |
| 5,981,481 | A | 11/1999 | Fearon et al. |
| 6,193,979 | B1 | 2/2001 | Rittershaus et al. |
| 6,316,604 | B1 | 11/2001 | Fearon et al. |
| 6,458,360 | B1 | 10/2002 | Fearon et al. |
| 6,713,606 | B1 | 3/2004 | Smith et al. |
| 2009/0118163 | A1 | 5/2009 | Gronski |

FOREIGN PATENT DOCUMENTS

WO    WO 89/09220 A1    10/1989

OTHER PUBLICATIONS

Servais et al ("Primary glomerulonephritis with isolated C3 deposits: a new entity wich shared common genetic risk factors with haemolytic uraemic syndrome", J Med Genet (2007), vol. 44:193-199).*
Mache et al. ("Complement Inhibitor Eculizumab in Atypical Hemolytic Uremic Syndrome", Clin J Am Soc Nephrol, vol. 4:1312-1316, published May 2009).*
Zimmerman et al. (Critical Care Medicine: Sep. 2000, vol. 28 (9) Abstract).*
Makrides et al. (Therapeutic Inhibition of the Complement System, Pharmacological Reviews; vol. 50 (1), 1998).*
Abrera-Abeleda et al., "Variations in the complement regulatory genes factor H (CFH) and factor H related 5 (CFHR5) are associated with membranoproliferative glomerulonephritis type II (dense deposit disease)", J. Med. Genet., 43: 582-589 (2006).
Appel et al., "Membranoproliferative glomerulonephritis type II (Dense Deposit Disease): an update", J. Am. Soc. Nephrol., 16: 1392-1403 (2005).
Ault, B.H., "Factor H and the pathogenesis of renal diseases", Pediatr. Nephrol., 14(10-11): 1045-1053 (2000).
Barbiano di Belgiojoso et al., "The prognostic value of some clinical and histological parameters in membranoproliferative glomerulonephritis (MPGN): report of 112 cases", Nephron., 19(5): 250-258 (1977).
Cameron et al., "Idiopathic mesangiocapillary glomerulonephritis. Comparison of types I and II in children and adults and long-term prognosis", Am. J. Med., 74(2): 175-192 (1983).
Delvaeye et al., "Thrombomodulin mutations in atypical hemolytic-uremic syndrome", N. Engl. J. Med., 361: 345-357 (2009).
Fakhouri et al., "Treatment with human complement factor H rapidly reverses renal complement deposition in factor H-deficient mice", Kidney International, 78: 279-286 (2010).
Fearon, D.T., "Identification of the membrane glycoprotein that is the C3b receptor of the human erythrocyte, polymorphonuclear leukocyte, B lymphocyte, and monocyte", J. Exp. Med., 152(1): 20 (1980).
Fearon et al., "Regulation of the amplification C3 convertase of human complement by an inhibitory protein isolated from human erythrocyte membrane", Proc. Natl. Acad. Sci. USA, 76(11): 5867-5871 (1979).
Fremeaux-Bacchi et al., "Mutations in complement C3 predispose to development of atypical hemolytic uremic syndrome", Blood, 112(13): 4948-4952 (2008).
Goicoechea de Jorge et al., "Gain-of-function mutations in complement factor B are associated with atypical hemolytic uremic syndrome", Proc. Natl. Acad. Sci., USA, 104(1): 240-245 (2007).
Habib et al., "Dense deposit disease: a variant of membranoproliferative glomerulonephritis", Kidney Int., 7(4): 204-215 (1975).
Habib et al., "Glomerular lesions in the transplanted kidney in children", Am. J. Kidney Disease, 10(3): 198-207 (1987).
Hogasen et al., "Hereditary porcine membranoproliferative glomerulonephritis type II is caused by factor H deficiency", J. Clin. Invest., 95(3): 1054-1061 (1995).
Iida et al., "Complement receptor is an inhibitor of the complement cascade", J. Exp. Med., 153: 1138 (1981).
Jozsi et al., "Attachment of the soluble complement regulator factor H to cell and tissue surfaces: relevance for pathology", Histol. Histopathol., 19(1): 251-258 (2004).
Moore et al., "Association of factor H autoantibodies with deletions of CFHR1, CFHR3, CFHR4, and with mutations in CFH, CFI, CD46, and C3 in patients with atypical hemolytic uremic syndrome", Blood, 115(2): 379-387 (2009).

(Continued)

*Primary Examiner* — James H Alstrum Acevedo
*Assistant Examiner* — Tara Martinez
(74) *Attorney, Agent, or Firm* — Leon R. Yankwich; David G. O'Brien; Yankwich & Associates, P.C.

(57) ABSTRACT

A method is disclosed for treating nephropathies involving undesired alternative pathway complement activation by administration of a complement inhibitory protein such as soluble complement receptor type I (sCR1).

19 Claims, 6 Drawing Sheets

(56) References Cited

OTHER PUBLICATIONS

Noris et al., "Atypical hemolytic-uremic syndrome", N. Engl. J. Med., 361(17): 1676-1687 (2009).

Orth et al., "The nephrotic syndrome", New Engl. J. Med., 338(17): 1202-1211 (1998).

Pickering et al., "Uncontrolled C3 activation causes membranoproliferative glomerulonephritis in mice deficient in complement factor H", Nat. Genet., 31(4): 424-428 (2002).

Pruitt et al., "The effect of soluble complement receptor type 1 on hyperacute allograft rejection", J. Surg. Res., 50(4): 350-355 (1991).

Pruitt et al., "The effect of soluble complement receptor type 1 on hyperacute xenograft rejection", Transplantation, 52 (5): 868-873 (1991).

Repik et al., "A transgenic mouse model for studying the clearance of blood-borne pathogens via human complement receptor 1 (CR1)", Clinical and Experimental Immunology, 140(2): 230-240 (2005).

Scesney et al., "A soluble deletion mutant of the human complement receptor type 1, which lacks the C4b binding site, is a selective inhibitor of the alternative complement pathway", Eur. J. Immunol., 26(8): 1729-1735 (1996).

Schwertz et al., "Complement analysis in children with idiopathic membranoproliferative glomerulonephritis: a long-term follow-up", Pediatr. Allergy Immunol., 12(3): 166-172 (2001).

Seed, "An LFA-3 cDNA encodes a phospholipid-linked membrane protein homologous to its receptor CD2", Nature, 329: 840-842 (1987).

Swainson et al., "Mesangiocapillary glomerulonephritis: a long-term study of 40 cases", J. Pathol., 141(4): 449-468 (1983).

Weisman et al., "Soluble human complement receptor type 1: in vivo inhibitor of complement suppressing post-ischemic myocardial inflammation and necrosis", Science, 249(4965): 146-151 (1990).

Wilson et al., "Characterization of human T lymphocytes that express the C3b receptor", J. Immunol., 131(2): 684-689 (1983).

Yeh et al., "Recombinant soluble human complement receptor type 1 inhibits inflammation in the reversed passive arthus reaction in rats", J. Immunol., 146(1): 250-256 (1991).

\* cited by examiner

TREATMENT OF CHRONIC NEPHROPATHIES USING SOLUBLE COMPLEMENT RECEPTOR TYPE I (SCR1)

CROSS-REFERENCE TO PRIORITY APPLICATIONS

This application claims priority to U.S. Provisional Appln. No. 61/383,004 filed Sep. 15, 2010, the contents of which are incorporated herein.

This invention was made with government support under grant DK074409 awarded by the National Institutes of Health. The government has certain rights in the invention.

FIELD OF THE INVENTION

The present invention relates to pharmaceutical compositions for treatment of diseases associated with dysregulation of the alternative pathway complement activation which ultimately harms kidney function, in particular atypical hemolytic uremic syndrome (aHUS) and dense deposit disease (DDD, also known as membrano-proliferative glomerulonephritis type II or MPGN2), as well as a recently described syndrome referred to as glomerulonephritis with isolated C3 deposits (GN-C3) or C3 glomerulopathy (C3G). Specifically, the invention relates to the use of pharmaceutical compositions comprising a soluble complement receptor type I (sCR1) to treat such diseases.

BACKGROUND OF THE INVENTION

The complement system comprises more than 40 different proteins directly or indirectly mediating attack and elimination of microbes, foreign particles and altered self cells via three different pathways of activation: classical pathway, alternative pathway, and lectin pathway (see, *The Complement System,* 2nd revised edition, Rother et al. (eds); Springer Verlag, 1998). The complement system is a major component of innate immunity and is a central host defense against infection. Activation of the complement cascade via the classical pathway, involving antigen-antibody complexes, by the lectin pathway, or by the alternative pathway, involving the recognition of certain cell wall polysaccharides, mediates a range of activities including lysis of microorganisms, chemotaxis, opsonization, stimulation of vascular and other smooth muscle cells, degranulation of mast cells, increased permeability of small blood vessels, directed migration of leukocytes, and activation of B lymphocytes and macrophages. The membrane attack complex (MAC) is the final product of the activated complement cascade. It is a lytic multi-protein complex that is lethal to pathogens and, at sublytic levels, causes the release of cytokines and growth factors such as beta-FGF and VEGF from nucleated cells (e.g., smooth muscle cells, endothelial cells).

Several human diseases are characterized by an unwanted activation of the complement cascade via one or more of these activation pathways, which is reflected by elevated levels of typical activation markers such as downstream components of the complement cascade, e.g., cleavage products of the complement system and inhibitor-protease complexes. Proteolytic cleavage of C3 by specific C3 convertases plays a major role in complement activation. C3 convertases generate forms of C3b, which represent a potential component of new C3 convertase molecules, thereby stimulating the cascade.

The protection of self-cells and tissue is normally tightly regulated by specific complement regulatory proteins or inhibitors, existing in the fluid-phase (soluble form) and/or in membrane-bound forms. The membrane-bound complement regulatory proteins include complement receptor type I (CR1 or CD35), which binds C3b and C4b, disassembles C3 convertases and permits C3b/C4b degradation by factor I; decay accelerating factor (DAF or CD55), which binds C3b and disassembles C3/C5 convertase; and membrane co-factor protein (MCP or CD46), which binds C3b and C4b to permit their degradation by factor I). In addition to the membrane-anchored complement regulatory proteins, the soluble regulatory protein Factor H acts as a potent protective factor for cells by attachment to the polyanionic surface of self cells, where it increases complement inhibitory potential (Jozsi et al., *Histol. Histopathol.,* 19:251-8 (2004)). This protective activity of Factor H is mainly achieved by its efficient reduction of the lifetime of the alternative C3 convertase C3bBb by (1) binding to the covalently bound C3b and displacing Bb (decay acceleration), and (2) catalyzing the permanent inactivation of C3b via proteolytic cleavage by the serine proteinase factor I (co-factor activity: generation of, e.g., iC3b, C3c). (*The Complement System,* 2nd revised edition, Rother et al. (eds); Springer Verlag, 1998; pp. 28, 34-7.) The activity of Factor H as co-factor for factor I in the outer phase of the surface layer (approx. 20-140 nm) is facilitated by binding of Factor H to surface-located proteoglycans by means of the C-terminal short consensus repeat (Jozsi et al. (2004), supra). The protective potential of Factor H limits locally the progression of the complement cascade. This is of particular importance for cells that express a low number of the membrane-anchored complement regulators, or for tissues which completely lack such complement regulatory proteins, such as the kidney glomerular basement membrane (Hogasen et al., *J. Clin. Invest.,* 95:1054-61 (1995)).

A significant reduction or absence of functional Factor H protein, i.e., due to reduced or eliminated Factor H expression, or mutation of the Factor H gene leading to production of mutant Factor H that is non-functional or has reduced functionality, has been demonstrated as one possible cause in diseases such as atypical hemolytic uremic syndrome (aHUS), dense deposit disease (DDD, also known as membranoproliferative glomerulonephritis type II or MPGN2), and glomerulonephritis with isolated C3 deposits (GN-C3, also sometimes referred to as C3 glomerulopathy, or C3G). These diseases ultimately harm kidney function. Since the glomerular membrane lacks endogenous complement regulatory membrane proteins, continuous cleavage of C3 occurs at this site, resulting in deposition of complement activation products, resulting in C3 convertase-mediated damage of the glomerular basement membranes and of epithelial tubules and endothelial cells, membrane thickening via deposition of extracellular matrix and/or components of the complement system (e.g., C3 cleavage products) and of antibodies, and, consequently, in defective filtration (proteinuria).

Dense deposit disease (DDD), also termed membranoproliferative glomerulonephritis type II or MPGN2, is a rare disease which is characterized by complement-containing dense deposits within the basement membrane of the glomerular capillary wall, followed by capillary wall thickening, mesangial cell proliferation and glomerular fibrosis (Ault, *Pediatr. Nephrol.,* 14:1045-53(2000)). Besides DDD, there are two other types of membranoproliferative glomerulonephritis, i.e., types I and III (MPGN1 and MPGN3, respectively). The membranoproliferative glomerulonephritides are diseases of diverse and often obscure etiology that account for 4% and 7% of primary renal causes of nephrotic syndrome in children and adults, respectively (Orth et al., *New Engl. J. Med.,* 338:1202-1211 (1998)). Membranoproliferative glomerulonephritis (MPGN) types I and III are variants of immune complex-mediated disease; MPGN type II, in contrast, has no known association with immune complexes (Appel et al., "Membranoproliferative glomerulonephritis type II (Dense Deposit Disease): an update," *J. Am. Soc. Nephrol.,* 16:1392-1403 (2005)).

DDD accounts for less than 20% of cases of MPGN in children and only a fractional percentage of cases in adults (Orth et al., 1998, supra; Habib et al., *Kidney Int.,* 7:204-15 (1975); Habib et al., *Am. J. Kidney Diseas.,* 10:198-207 (1987)). Both sexes are affected equally, with the diagnosis usually made in children between the ages of 5-15 years who present with non-specific findings like hematuria, proteinuria, acute nephritic syndrome or nephrotic syndrome (Appel et al., 2005, supra). More than 80% of patients with DDD are also positive for serum C3 nephritic factor (C3NeF), an autoantibody directed against C3bBb, the convertase of the alternative pathway of the complement cascade (Schwertz et al., *Pediatr. Allergy Immunol.,* 12:166-172 (2001)). C3NeF is found in up to one-half of persons with MPGN types I and III and also in healthy individuals, making the electron microscopic demonstration of dense deposits in the glomerular basement membrane (GBM) necessary for a definitive diagnosis of DDD (Appel et al., 2005, supra). This morphological hallmark is characteristic of DDD and is the reason "dense deposit disease" or "DDD" have become the more common terms for this MPGN.

C3NeF autoantibodies persists throughout the disease course in more than 50% of patients with DDD (Schwertz et al., 2001). Its presence is typically associated with evidence of complement activation, such as a reduction in CH50, decrease in C3, increase in C3dg/C3d, and persistently high levels of activation of the alternative pathway of the complement cascade. In DDD, C3NeF binds to C3bBb (or to the assembled convertase) to prolong the half-life of this enzyme, resulting in persistent C3 consumption that overwhelms the normal regulatory mechanisms to control levels of C3bBb and complement activation (Appel et al., 2005, supra). Most DDD patients do not have disease-causing mutations in Factor H, however, several alleles of both Factor H and the complement Factor H-related 5 gene (CFHR5) are preferentially associated with DDD (Abrera-Abeleda, M. A., et al., *Journal of Medical Genetics,* 43:582-589 (2006)).

Spontaneous remissions of DDD are uncommon (Habib et al., 1975, supra; Habib et al., 1987, supra; Cameron et al., *Am. J. Med.,* 74:175-192 (1983)). The more common outcome is chronic deterioration of renal function leading to end-stage renal disease (ESRD) in about half of patients within 10 years of diagnosis (Barbiano di Belgiojoso et al., *Nephron.,* 19:250-258 (1977)); Swainson et al., *J. Pathol.,* 141:449-468 (1983)). In some patients, rapid fluctuations in proteinuria occur with episodes of acute renal deterioration in the absence of obvious triggering events; in other patients, the disease remains stable for years despite persistent proteinuria.

Atypical hemolytic-uremic syndrome (aHUS) consists of the triad of microangiopathic hemolytic anemia, thrombocytopenia, and renal failure. aHUS, although rare, is a severe disease with death rates up to 25% in the acute phase and 50% developing end-stage renal disease (Noris, M., et al., *N. Engl. J. Med.,* 361:1676-1687 (2009)).

Research has linked atypical haemolytic-uremic syndrome to uncontrolled activation of the complement system. Approximately half of the patients with aHUS have mutations in CFH, CFI and MCP, encoding the complement regulatory proteins complement factor H, factor I and membrane cofactor protein, respectively (www.FH-HUS.org) (Noris, M., et al., 2009, supra). Gain-of-function mutations in key proteins of the alternative pathway cascade, complement factor B (CFB) and C3 have also been reported (Goicoechea de Jorge, E., et al., *Proc. Natl. Acad. Sci. USA,* 104:240-245 (2007); Fremeaux-Bacchi, V. et al., *Blood,* 112:4948-4952 (2008)). More recently, mutations in the gene encoding thrombomodulin (THBD), a membrane-bound glycoprotein with anticoagulant properties that modulates complement activation on cell surfaces, have also been associated with aHUS (Delvaeye, M., et al., *N. Engl. J. Med.,* 361:345-357 (2009)). Finally, aHUS associated with anti-CFH autoantibodies has been described in sporadic forms mostly in association with deficiency of factor H related proteins 1 and 3 (Moore, I., et al., *Blood,* 115:379-387 (2009)).

In vitro functional tests with recombinant or plasma-purified CFH, MCP, CFI and THBD all documented that aHUS-associated mutations impair the capacity of regulatory proteins to control the activity of the alternative pathway of complement on endothelial cell surface (Noris, M., et al., 2009, supra). On the other hand, gain of function mutations in CFB and C3 resulted in hyperfunctional components of the C3 convertase that caused complement deposition on cell surface in vitro (Goicoechea de Jorge, E., et al., 2007, supra; Fremeaux-Bacchi, V. et al., 2008, supra). These findings indicate that aHUS is a disease of excessive complement activation on endothelial cells, which eventually results in renal microvascular thrombosis.

Factor H replacement therapy, inter alia, has been proposed for aHUS and DDD patients (see, e.g., US Pat. Publication 2009-0118163), however difficulties arise where the normal levels of a non-functional mutant Factor H are underlying the disease. It was not previously known whether addressing the continuous activation of complement via the alternative pathway would be a viable therapy, and a persistent need for new therapeutic approaches is evident.

SUMMARY OF THE INVENTION

The present invention relates to the use of a soluble complement receptor type I protein for the therapeutic treatment of nephropathies, in particular atypical hemolytic uremic syndrome (aHUS), dense deposit disease (DDD, also known as membranoproliferative glomerulonephritis type II or MPGN2), and glomerulonephritis with isolated C3 deposits (GN-C3, also sometimes referred to as C3 glomerulopathy, or C3G).

Thus, in one aspect, the present invention provides a new pharmaceutical composition for the treatment of aHUS, DDD or GN-C3 comprising an amount of a soluble CR1 protein, effective to inhibit complement and a pharmaceutically acceptable vehicle.

In another aspect, the present invention relates to the use of a soluble complement receptor type I (sCR1) polypeptide in the treatment of a nephropathy characterized by undesired alternative pathway complement activation.

In preferred aspects of the invention, the sCR1 polypeptide used in the methods herein is selected from a fragment of human CR1 comprising at least short consensus repeats 8-11; a fragment of human CR1 comprising at least short consensus repeats 15-18; a soluble CR1 polypeptide comprising human CR1 short consensus repeats 8-11 and 15-18; a fragment of human CR1 comprising long homologous repeat B; a fragment of human CR1 comprising long homologous repeat C; a fragment of human CR1 comprising long homologous repeats B and C; a fragment of human CR1 comprising long homologous repeats B, C and D; a fragment of human CR1 comprising at least long homologous repeats A and B; a fragment of human CR1 comprising long homologous repeats A, B and C; a fragment of human CR1 comprising long homologous repeats A, B, C and D; a fragment of human CR1 comprising the extracellular domain of CR1; a fragment of human CR1 comprising the extracellular domain of CR1 and having the N-terminal LHR A deleted (sCR1[desLHR-A]); a soluble CR1 polypeptide having modified glycosylation to improve serum half-life in vivo; a soluble CR1 polypeptide having glycosylation modified to exhibit sialyl Lewis X moieties (sCR1-sLe$^x$); a soluble CR1 construct having two or more CR1 polypeptide moieties linked to a carrier molecule; and combinations thereof.

In another aspect of the invention, the sCR1 polypeptide or fragment thereof used the in the methods disclosed herein exhibits a complement regulatory activity selected from the group consisting of: (i) the ability to bind C3b; (ii) the ability to bind C4b; (iii) the abilities to bind C3b and to bind C4b; (iv) factor I cofactor activity; (v) the ability to inhibit classical C3 convertase activity; (vi) the ability to inhibit alternative C3 convertase activity; (vii) the ability to inhibit classical C5 convertase activity; (viii) the ability to inhibit alternative C5 convertase activity; (ix) the ability to inhibit neutrophil oxidative burst; (x) the ability to inhibit complement-mediated hemolysis; (xi) the ability to inhibit C3a production; and (xii) the ability to inhibit C5a production. In yet another aspect of the invention, the sCR1 polypeptide or fragment thereof exhibits combinations of the above activities.

In another aspect, the sCR1 polypeptide or fragment thereof used the in the methods disclosed herein exhibits ability to inhibit complement activation via both the classical activation pathway and the alternative activation pathway.

Another aspect of the invention relates to the use of a soluble complement receptor type I (sCR1) polypeptide in the treatment of a nephropathy in a mammal, including humans, characterized by undesired alternative pathway complement activation.

In yet another aspect of the invention, the nephropathy characterized by undesired alternative pathway complement activation results in C3 deposition in kidney tissue.

In one aspect of the invention, the use of the sCR1 polypeptide in the treatment of a nephropathy described herein results in a reduction of further C3 deposition in kidney tissue and/or at least partially reverses existing C3 deposition and reduces further C3 deposition in kidney tissue.

In yet another aspect of the invention, the use of a soluble complement receptor type I (sCR1) polypeptide in the treatment of a nephropathy characterized by undesired alternative pathway complement activation reduces kidney damage, reduces further kidney damage, and/or at least partially reverses existing kidney damage.

In another aspect of the invention, the use of a soluble complement receptor type I (sCR1) polypeptide in the treatment of a nephropathy characterized by undesired alternative pathway complement activation reduces deterioration in renal function and/or improves renal function. In one aspect of the invention, the improved renal function is indicated by one or more of i) reduced proteinuria, ii) reduced serum creatinine, and/or iii) improved glomerular filtration rate.

In another aspect of the invention, the use of a soluble complement receptor type I (sCR1) polypeptide in the treatment of a nephropathy characterized by undesired alternative pathway complement activation increases serum levels of C3.

Another aspect of the invention relates to a method for treating DDD comprising administration of an amount of a soluble CR1 protein effective to inhibit alternative pathway complement activation to a mammalian subject suffering from DDD. Another aspect of the invention relates to a method for treating aHUS comprising administration of an amount of a soluble CR1 protein effective to inhibit alternative pathway complement activation to a mammalian subject suffering from aHUS. Another aspect of the invention relates to a method for treating GN-C3 comprising administration of an amount of a soluble CR1 protein effective to inhibit alternative pathway complement activation to a mammalian subject suffering from GN-C3.

Another aspect of the invention relates to a method for treating DDD comprising systemic administration of an amount of a soluble CR1 protein effective to inhibit complement activity to a mammalian subject suffering from DDD. In this aspect, administration of the soluble CR1 protein may be intravenous (IV), subcutaneous (SC), intramuscular (IM), intra-arterial, intraperitoneal (IP), intrathecal, pulmonary, or oral. Another aspect of the invention relates to a method for treating aHUS comprising systemic administration of an amount of a soluble CR1 protein effective to inhibit complement activity to a mammalian subject suffering from aHUS. In this aspect, administration of the soluble CR1 protein may be intravenous (IV), subcutaneous (SC), intramuscular (IM), intra-arterial, intraperitoneal (IP), intrathecal, pulmonary, or oral.

Yet another aspect of the invention relates to a method for treating GN-C3 comprising systemic administration of an amount of a soluble CR1 protein effective to inhibit complement activity to a mammalian subject suffering from GN-C3. In this aspect, administration of the soluble CR1 protein may be intravenous (IV), subcutaneous (SC), intramuscular (IM), intra-arterial, intraperitoneal (IP), intrathecal, pulmonary, or oral.

Pharmaceutical compositions for use in treating DDD, GN-C3 or aHUS comprising a soluble complement receptor type I and a pharmaceutically acceptable diluent, carrier or excipient are also contemplated. Use of a soluble complement receptor type I in the manufacture of a medicament for the treatment of DDD, GN-C3 or aHUS is also contemplated.

DETAILED DESCRIPTION

Figure 1:
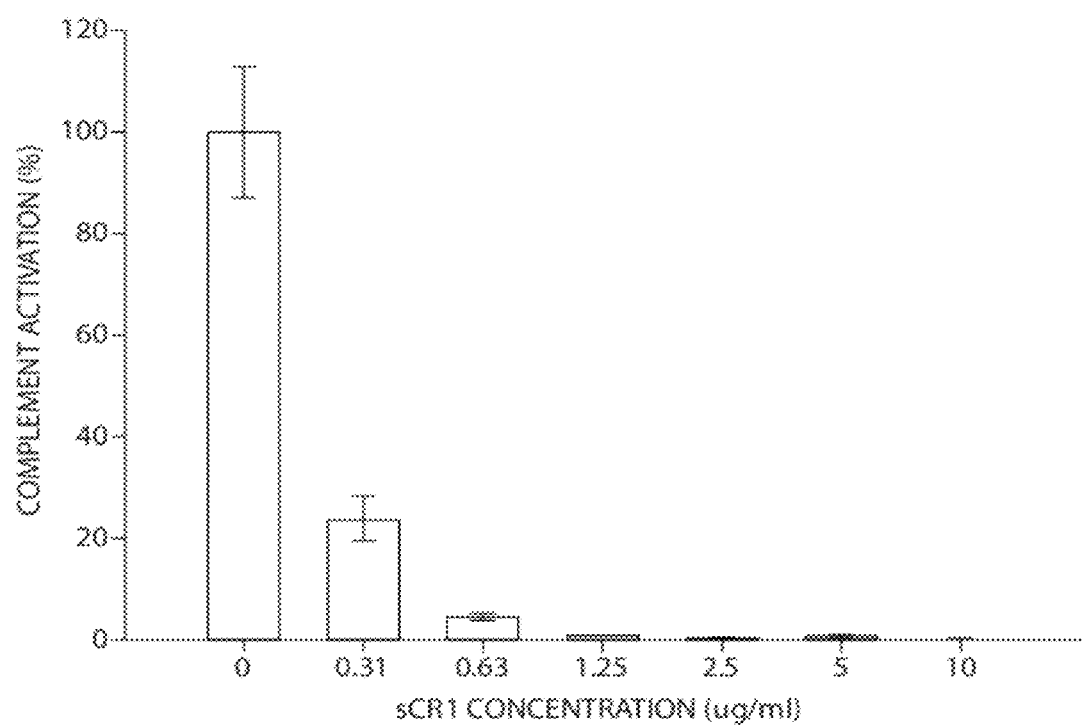
FIG. 1 is a graph showing the dose-dependent inhibition of alternative pathway (AP) complement activation by sCR1.

The present invention is based on the important and surprising discovery that administration of a complement inhibitory protein, in particular soluble CR1, is effective in inhibiting alternative pathway complement activity in patients with chronic nephropathies/glomerulopathies, in particular atypical hemolytic uremic syndrome (aHUS), dense dense deposit disease (DDD, also known as membranoproliferative glomerulonephritis type II or MPGN2), and glomerulonephritis with isolated C3 deposits (GN-C3, also sometimes referred to as C3 glomerulopathy or C3G).

In order that the invention may be more fully understood, the following terms are defined.

The term "nephropathy" or "nephrosis" as used herein refers to damage to or disease or disorder of the kidney, including diseases/disorders associated with undesired alternative pathway complement activation and/or deposition of complement activation products in kidney tissue, including atypical hemolytic uremic syndrome (aHUS) and/or dense deposit disease (DDD) and/or glomerulonephritis with isolated C3 deposits (GN-C3).

The term "complement inhibitory protein" as used herein refers to any of the complement regulatory proteins that have a negative regulatory activity on complement activation. Complement inhibitory proteins useful in the present invention include, specifically, soluble complement receptor type I (sCR1), C4-binding protein (C4-BP), decay accelerating factor (DAF), membrane cofactor protein (MCP), and Factor H.

As used herein, the terms "soluble complement receptor type I", "soluble CR1 polypeptides" or "soluble CR1" or "sCR1" will be used to refer to portions of full-length human CR1 protein which, in contrast to the native CR1 proteins, are not expressed on the cell surface as transmembrane proteins but nevertheless exhibit a complement regulatory activity such as C3b binding, C4b binding, the ability to inhibit the classical complement activation pathway and/or the alternative complement activation pathway, and/or the lectin complement activation pathway, etc. In particular, CR1 polypeptides which substantially lack a transmembrane region, or, preferably, which comprise all or part of the extracellular domain of CR1 and retain a complement regulatory activity, are soluble CR1 polypeptides. In a preferred embodiment, the soluble CR1 polypeptides useful in the present invention are secreted by a cell in which they are expressed. Suitable soluble CR1 polypeptides and preparations are described in detail, e.g., in U.S. Pat. No. 5,981,481; U.S. Pat. No. 5,456,909; and U.S. Pat. No. 6,193,979, which are incorporated herein by reference. Soluble CR1 polypeptides having at least one C3b/C4b binding site intact are preferred, as such molecules have the ability to block complement activation via the classical activation pathway and the alternative activation pathway both. Reference to specific complement inhibitory proteins includes fragments of such proteins produced by truncation or splicing-out of unwanted polypeptide segments, so long as complement regulatory activity is retained. Derivatives made by one or more amino acid substitutions or linking to other structures such as carrier proteins or immunoglobulin constant regions are also contemplated, again so long as complement inhibitory activity is retained. In particular, soluble CR1 polypeptides having at least one of the two C3b/C4b binding sites (specifically, short consensus repeats (SCRs) 8-11 and 15-18) intact are preferred, because such molecules will retain the ability to block complement activation via the alternative complement pathway.

Special mention is made of a soluble CR1 polypeptide having glycosylation modified to exhibit sialyl Lewis X moieties (sCR1-sLe$^x$), as described in U.S. Pat. No. 6,193,979; novel glycoform preparations of soluble CR1 having an increased in vivo half-life described in U.S. Pat. No. 5,456,909; and soluble constructs having two or more CR1 moieties linked to a carrier molecule, e.g., an sCR1-F(ab)2 fusion, as described in U.S. Pat. No. 6,458,360. Also contemplated are soluble CR1 polypeptides having at least one of the C3b or C4b binding sites intact covalently linked to lipopeptides to facilitate localization on cell surfaces, as disclosed in U.S. Pat. No. 6,713,606. More preferably, the method of the invention utilizes a polypeptide comprising the extracellular domain of mature human CR1 (SEQ ID NO:1).

As used herein, the terms "treatment" or "treating" refers to any regimen that alleviates one or more symptoms of a disease or disorder, that inhibits progression of a disease or disorder, that arrests progression or reverses progression (causes regression) of a disease or disorder, or that prevents onset of a disease or disorder. Treatment includes prophylaxis and includes but does not require cure of a disease or disorder.

As used herein, the terms "disease" and "disorder" have the meaning generally known and understood in the art and comprise any abnormal condition in the function or well being of a host individual. A diagnosis of a particular disease or disorder, such as atypical hemolytic uremic syndrome (aHUS) and/or dense deposit disease (DDD) and/or glomerulonephritis with isolated C3 deposits (GN-C3) by a healthcare professional may be made by direct examination and/or consideration of results of one or more diagnostic tests.

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or "comprises") one or more named elements or steps also describes the corresponding, more limited, composition or method "consisting essentially of" (or "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or "consists of") the named elements or steps to the exclusion of any other unnamed element or step. In any composition or method disclosed herein, known or disclosed equivalents of any named essential element or step may be substituted for that element or step.

The definitions of other terms used herein are those understood and used by persons skilled in the art and/or will be evident to persons skilled in the art from their usage in the text.

The method of this invention can be practiced by using any soluble complement receptor type I polypeptide which is effective to block alternate pathway complement activation. Such complement inhibitory proteins include, for example, soluble complement receptor type I (sCR1) of SEQ ID NO:1, i.e., comprising the extracellular domain of human CR1, or fragments of CR1 that retain complement inhibiting properties, such as the ability to inhibit complement activation, to bind C3b, or to bind both C3b and C4b, or factor I co-factor activity. Preferably, the complement inhibitory protein used in the methods described herein is a soluble (non-membrane-bound) form of human CR1 comprising at least long homologous repeats (LHRs) B and/or C, preferably both LHRs B and C, more preferably long homologous repeats A, B, and C or A, B, C, and D, and most preferably substantially the entire extracellular domain of human CR1 or the molecule sCR1

[desLHR-A], which is the extracellular domain of CR1 including the LHRs BCD but omitting the N-terminal LHR A (see, Scesney, S. M. et al, *Eur. J. Immunol.*, 26:1729-35 (1996)). Suitable soluble CR1 polypeptides and preparations are described in detail, e.g., in U.S. Pat. No. 5,981,481; U.S. Pat. No. 5,456,909; and U.S. Pat. No. 6,193,979. Modified sCR1 molecules having, for example, a modified glycosylation, e.g., to improve serum half-life, such as those described in U.S. Pat. No. 5,456,909 may also be used. Soluble CR1 polypeptides having glycosylation modified to exhibit sialyl Lewis X moieties (designated sCR1-sLe$^x$), as described in U.S. Pat. No. 6,193,979, may also be used. And soluble constructs having two or more CR1 moieties linked to a carrier molecule, e.g., an sCR1-F(ab)2 fusion, as described in U.S. Pat. No. 6,458,360, may also be used.

As discussed more fully below, it has been demonstrated herein that administration of sCR1 alleviates the effects of undesirable alternative pathway complement activation, in particular in nephropathic diseases such as atypical hemolytic uremic syndrome (aHUS), dense deposit disease (DDD), or glomerulonephritis with isolated C3 deposits (GN-C3). We have thus discovered that administration of a complement inhibitory protein to a subject in a relevant aHUS or MPGN2 model reduces and/or ameliorates the pathogenesis of massive activation of the alternative pathway and terminal complement cascade, with subsequent deposition of complement activation products (iC3b, C3c, C3d, sMAC) in the glomerular basement membrane. The effects of sCR1 in nephropathic diseases has been demonstrated in vivo, which demonstrates an important aspect previously unknown, namely, whether sCR1 could be delivered to affect C3 deposition at particular tissues lacking complement regulatory proteins, such as kidney glomerular basement membrane, whether the regulatory activity of sCR1 could persist for a meaningful period in vivo to alleviate the effects of unregulated complement activation and such outward indicators as C3 deposition in kidney tissues, and whether administration of sCR1 could be effective at a dosage level that would make sCR1 a realistic candidate as a therapeutic.

It has also now been demonstrated that sCR1 can effectively compete with C3Nef autoantibodies and counterbalance C3Nef-mediated complement activation that occurs in about 85% of DDD patients.

The human C3b/C4b receptor, termed complement receptor type I (CR1) or CD35, is naturally present on the membranes of erythrocytes, monocytes/macrophages, granulocytes, B cells, some T cells, splenic follicular dendritic cells, and glomerular podocytes. (Fearon, 1980, *J. Exp. Med.*, 152: 20, Wilson, J. G., et al., 1983, *J. Immunol.*, 131: 684). CR1 specifically binds C3b, C4b, iC3b and iC4b.

CR1 can inhibit the classical and alternative pathway C3/C5 convertases and act as a cofactor for the cleavage of C3b and C4b by factor I, indicating that CR1 also has complement regulatory functions in addition to serving as a receptor. (Fearon, D. T., 1979, *Proc. Natl. Acad. Sci. U.S.A.*, 76: 5867; Iida, K. I. and Nussenzweig, V., 1981, *J. Exp. Med.*, 153: 1138.) In the alternative pathway of complement activation, the bimolecular complex C3bBb is a C3 protease (convertase). CR1 can bind to C3b thereby promoting the dissociation of fragment Bb from the complex. In the alternative pathway of complement activation, the tri-molecular complex C3bC3bBb is a C5 protease (convertase). CR1 can bind to C3bC3b thereby promoting the dissociation of fragment Bb from the complex. Furthermore, binding of C3b to CR1 renders C3b susceptible to irreversible proteolytic inactivation by factor I, resulting in the production of inactivated derivatives of C3b (namely, iC3b, C3d and C3dg). In the classical pathway of complement activation, the bimolecular complex C4bC2a is the C3 convertase. CR1 binds to C4b thereby promoting the dissociation of C2a from the complex. In the classical pathway of complement activation, the complex C3bC4bC2a is the C5 convertase. CR1 binds to C4b and/or C3b thereby promoting the dissociation of C2a from the complex. The binding renders C4b and/or C3b susceptible to irreversible proteolytic inactivation by factor I. Finally, the lectin pathway (also called the mannose binding lectin or MBL pathway) feeds into the classical pathway upstream of the C3 convertase. Thus, CR1 inhibits lectin pathway activation through its inhibitory activities on the classical pathway at the C3 and C5 activation steps.

Factor H has some of the same properties exhibited by CR1 but is not effective to block both activation pathways. Factor H has decay accelerating activity and factor I co-factor activity in the alternative pathway only. In addition, the activity of Factor H is restricted to non-activating surfaces. This is an important distinction with respect to CR1, which is active both on activating and non-activating surfaces and is therefore more suitable for use under conditions of an ongoing disease. Activating surfaces would include, e.g., the presence of necrotic and inflamed tissue.

Several soluble (non-membrane bound) fragments of CR1 have been generated via recombinant DNA procedures by eliminating the transmembrane and cytoplasmic regions from the DNAs being expressed. See, e.g., Fearon et al., Intl. Patent Publn. WO 89/09220, Oct. 5, 1989. The soluble CR1 fragments are functionally active, i.e., retaining the ability to bind C3b and/or C4b, inhibiting complement activation, and demonstrating factor I co-factor activity, depending upon the native CR1 regions the CR1 fragments contain. Such constructs inhibit in vitro the consequences of complement activation such as neutrophil oxidative burst, complement mediated hemolysis, C3a and C5a production, and the production of C5b-9 (MAC). A soluble construct, sCR1/pBSCR1c, also has demonstrated in vivo activity in a reversed passive Arthus reaction (Yeh et al., 1991, *J. Immunol.*, 146:250), suppressed post-ischemic myocardial inflammation and necrosis (Weisman et al., 1990, *Science*, 249: 146-151) and extended survival rates following transplantation (Pruitt et al., 1991, *J. Surg. Res.*, 50: 350; Pruitt et al., 1991, *Transplantation*, 52: 868).

The complete cDNA coding sequence and amino acid sequence of the human CR1 protein is described in U.S. Pat. No. 5,981,481, which is incorporated herein by reference. The isolation of the full-length CR1 gene, expression and purification of the full-length protein and active fragments thereof, and demonstration of activity in the full-length protein and fragments derived from the full-length protein, are described in U.S. Pat. No. 5,981,481.

The complement inhibitory proteins such as sCR1 that are useful in the methods of the present invention are advantageously produced in quantity using recombinant DNA technology to express the protein in a host cell, such as bacterial cells, mammalian cells, or even plant cells. For the complement inhibitory proteins contemplated herein, mammalian host cells, such as Chinese Hamster ovary (CHO) cells, African Green Monkey kidney (COS) cells, or human cells, retina-derived cells (e.g., PER.C6 cells) being preferred. Yeast expression, *E. coli* expression, baculovirus expression, and plant expression are also contemplated, where non-mammalian glycosylation patterns do not have a significant impact on biological function or pharmacokinetics. Other expression systems for the production of recombinant proteins will also be useful for the production of complement receptor type I polypeptides contemplated herein. The isolated gene encoding the desired protein can be inserted into an appropriate cloning vector. A large number of vector-host systems known in the art may be used. Possible vectors include, but are not limited to, plasmids or modified viruses. The vector system must be compatible with the host cell used. Such vectors include, but are not limited to, bacteriophages such as lambda derivatives, or plasmids such as pBR322, pUC or CDM8 plasmids (Seed, 1987, *Nature*, 329: 840-842) or derivatives of those well-known vectors. Recombinant molecules can be introduced into host cells via transformation, transfection, infection, electroporation, etc.

Recombinant cells producing a preferred form of sCR1 are deposited with the American Type Culture Collection, Rockville, Md. (accession no. CRL 10052). The deposited cells are a Chinese Hamster ovary cell line DUX B11 carrying plasmid pBSCR1c/pTCSgpt clone 35.6, encoding the extracellular domain of human CR1. Such sCR1 polypeptide in purified form is produced under the product designation TP10 and also by the designation CDX-1135 by Celldex Therapeutics, Inc. (Needham, Mass.).

After expression in a host cell, the soluble CR1 molecules may be isolated and purified by standard methods including chromatography (e.g., ion exchange, affinity, and sizing column chromatography, high pressure liquid chromatography), centrifugation, differential solubility, or by any other standard technique for the purification of proteins. Preferred purification methods are described in U.S. Pat. No. 6,316,604, U.S. Pat. No. 5,252,216, and U.S. Pat. No. 5,840,858, which are incorporated herein by reference.

Soluble CR1 proteins are therapeutically useful in the modulation of complement-mediated diseases, that is, diseases or conditions characterized by inappropriate or undesired complement activation. A soluble CR1 protein or fragment which can bind C3b and/or retains the ability to inhibit the alternative or classical C3 or C5 convertases, and/or retains factor I cofactor activity, can be used in the methods and uses disclosed herein. In the present invention, we have demonstrated that soluble CR1 can be used to ameliorate or inhibit undesirable complement activity in the pathogenesis of nephropathies caused by DDD and/or aHUS.

In the method of the invention, a soluble CR1 polypeptide is administered to a subject who suffers from aHUS, DDD, and/or GN-C3 in order to attenuate complement activation and its role in the pathogenesis in persistent reduction in serum C3 and deposition of complement activation products, resulting in C3 convertase-mediated damage of the glomerular basement membranes and of epithelial tubules and endothelial cells, membrane thickening via deposition of extracellular matrix and/or components of the complement system (e.g., C3 cleavage products) and of antibodies, and, consequently, in defective filtration (proteinuria).

In a method of treating DDD, aHUS, or GN-C3 according to the invention, a therapeutically active amount of a soluble complement receptor type I polypeptide is administered to a mammalian subject in need of such treatment. The preferred subject is a human. The amount administered should be sufficient to inhibit complement activation and/or restore normal alternative pathway regulation. The determination of a therapeutically effective dose is within the capability of practitioners in this art, however, as an example, in embodiments of the method described herein utilizing systemic administration of sCR1 for the treatment of DDD, an effective human dose will be in the range of 0.1-150 mg/kg; preferably 1-100 mg/kg, more preferably 3-75 mg/kg, most preferably 5-60 mg/kg patient body weight (e.g., 5 mg/kg, 10 mg/kg, 25 mg/kg, 50 mg/kg, etc.). The route of administration may affect the recommended dose. Repeated systemic doses are contemplated in order to maintain an effective level, e.g., to attenuate or inhibit complement activation in a patient's system, depending on the mode of administration adopted.

Soluble CR1 may be used in combination or alternating with the administration of other therapeutics prescribed for DDD and/or aHUS and/or GN-C3.

For administration, the sCR1 or other therapeutic protein may be formulated into an appropriate pharmaceutical composition. Such a composition typically contains a therapeutically active amount of the sCR1 or other protein and a pharmaceutically acceptable excipient or carrier such as saline, buffered saline, salt solutions (e.g., BSS®), phosphate buffers, dextrose, or sterile water. Compositions may also comprise specific stabilizing agents such as sugars, including mannose and mannitol.

Various delivery systems are known and can be used for delivery of complement inhibitory proteins such as sCR1 polypeptides in accordance with this invention, e.g., encapsulation in liposomes, microparticles, or microcapsules. Suitable modes of administration include but are not limited to intradermal, intramuscular, intraperitoneal, intravenous, subcutaneous, intrathecal, or epidural injection, and oral or pulmonary delivery.

Pharmaceutical compositions containing one or more complement inhibitory proteins for use in the present invention may be formulated in accordance with routine procedures as a pharmaceutical composition for systemic administration to an individual suffering from DDD and/or aHUS and/or GN-C3. Typically compositions for systemic administration are solutions in sterile aqueous buffer. Where necessary, the composition may also include a solubilizing agent and a local anesthetic such as lidocaine to ease pain at the site of injection. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by injection, an ampoule of sterile water for injection or saline may be provided so that the ingredients may be mixed prior to administration.

A pharmaceutical pack comprising one or more containers filled with one or more of the ingredients of the pharmaceutical composition is also contemplated.

The following examples illustrate the methods of the present invention. They are provided by way of illustration and not for purposes of limitation.

EXAMPLE 1

Recombinant soluble complement receptor type I (sCR1) consisting of the extracellular portion of human CR1, produced in CHO cells, was used in the following experiments. The sCR1 was obtained from Celldex Therapeutics, Inc. (Needham, Mass.).

Complement Activity Assay

Alternative pathway (AP) complement activity was evaluated in the fluid phase using the Wieslab complement AP assay kit (Wieslab AB, Lund, Sweden). This method combines principles of the hemolytic assay for complement activation with the use of labeled antibodies specific for a neoantigen produced as a result of complement activation. The amount of neoantigen generated is proportional to the functional activity of the alternative pathway.

Twenty (20) microliters of pooled normal serum (Innovative research, Cat #IPLA-CSER, Novo, Mich.) was diluted in 340 µl of diluents (Wieslab complement AP assay kit;

Wieslab AB, Lund, Sweden) containing specific blockers to ensure that only the alternative pathway is activated. Soluble CR1 polypeptide (TP10, Celldex Therapeutics, Inc., Needham, Mass.) was added to a final concentration of 10 µg/ml, 5 µg/ml, 2.5 µg/ml, 1.25 µg/ml, 0.63 µg/ml, 0.31 µg/ml or 0 µg/ml. The mixture was then incubated on ice for 15 minutes; thereafter, each diluted serum was transferred in 100 microliter aliquots to microtiter wells. Activation was initiated during incubation of diluted serum in microtiter wells coated with specific complement activators of the alternative pathway, i.e., LPS (lipopolysaccharides). The wells were washed with the provided buffer and C5b-9 (MAC) was detected using the provided phosphatase-labeled antibody to the neoantigen that is exposed during MAC formation.

Data showed that sCR1 strongly inhibits fluid phase activation of the alternative pathway in a dose-dependent manner (see, FIG. 1).

Hemolytic Assay

The sheep erythrocyte lysis assay measures complement-mediated lysis of sheep erythrocytes secondary to activation of the alternative pathway on a cell surface. Sheep erythrocytes generally act as non-activators of complement-mediated lysis in human serum. A small number of C3b molecules spontaneously generated through alternative pathway tickover are deposited on the surface of sheep erythrocytes. In normal human serum, factor H binds to C3b molecules through N-terminal domains and to sheep erythrocytes through C-terminal domains. These interactions protect sheep erythrocytes from complement and no lysis is observed.

Hemolysis was observed 30 minutes after mixing 20 microliters of patient A serum (FIG. 2, aHUS, dark blue) and sheep erythrocytes (50 µl, $1\times10^8$/ml) in the presence of $Mg^{++}$/EGTA (AP activation possible) at 37° C. In parallel tests, various amounts of sCR1 (to final concentrations 0 µg/ml, 10 µg/ml, 20 µg/ml, 30 µg/ml, 40 µg/ml) were added to the same amount serum (20 µl) from patient A before adding sheep erythrocytes (50 µl, $1\times10^8$/ml) and incubating for 15 minutes on ice. Hemolysis was greatly reduced by the addition of sCR1 (see, FIG. 2).

Figure 2:
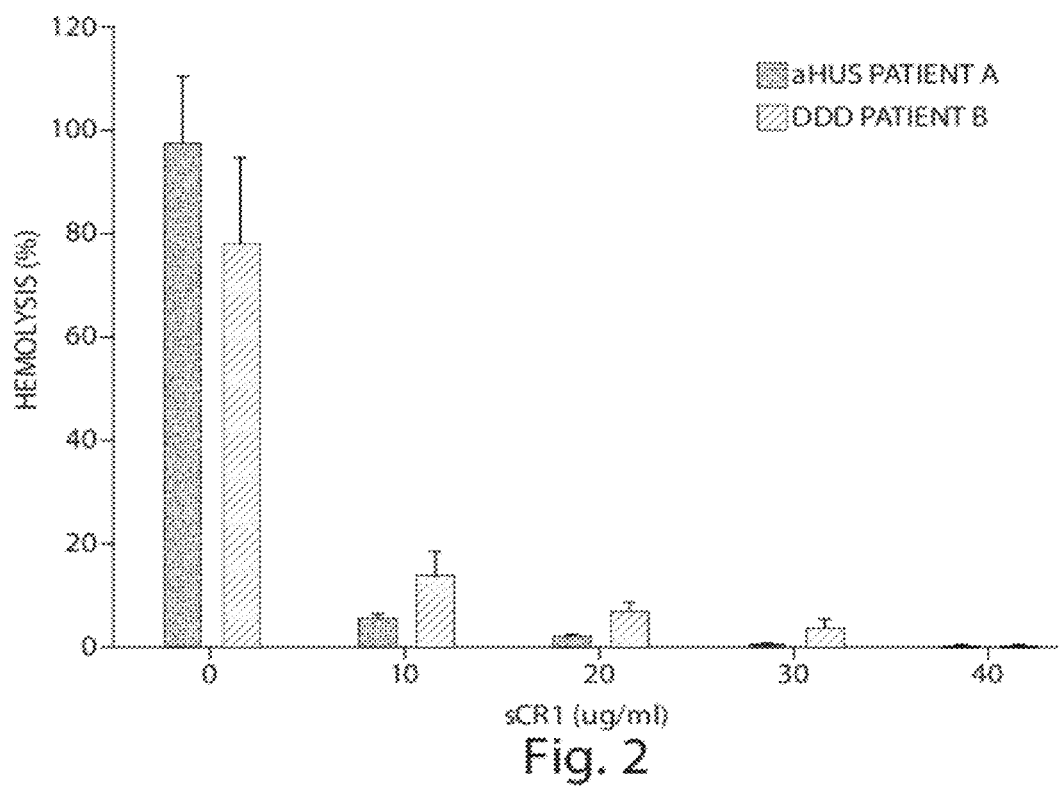
FIG. 2 is a graph showing the results of in vitro hemolytic assays in a patient with aHUS and a patient with DDD, showing that sCR1 is a potent inhibitor of C3 convertase activity in both patients, and even in the presence of C3NeF in the DDD patient.

Patient B has dense deposit disease (DDD) and very strong C3NeF activity, which causes uncontrolled alternative pathway activation with massive C3 consumption. As a consequence, alternative pathway complement factors are totally consumed. To test whether sCR1 can prevent C3NeF from stabilizing C3 convertase, 10 µl of patient B's serum were added to 10 µl of sheep erythrocytes ($1\times10^9$/ml) coated with pre-formed C3 convertase. Pre-formed C3 convertase was allowed to decay at 30° C. (water bath) for 20 minutes. The pre-formed C3 convertase was made by adding normal human serum to sheep erythrocytes and incubating first at room temperature (water bath) for 8 minutes and then on ice for 40 minutes. Sheep RBCs were lysed in the prolonged presence of C3 convertase. Hemolysis was assayed by adding rat serum (1:5 diluted in GVB-EDTA buffer) as a source of C3-9 (FIG. 2, DDD, light blue). In parallel tests, various amounts of sCR1 (to final concentrations 0 µg/ml, 10 µg/ml, 20 µg/ml, 30 µg/ml, 40 µg/ml) were added to the patient serum before mixing with sheep erythrocytes and incubating on ice for 15 minutes. Data showed that sCR1 suppressed C3NeF activity in a dosage-dependent manner (see, FIG. 2). Repetition of this experiment with sera from ten DDD patients showed similar results.

The results of the in vitro hemolytic assays in a patient with aHUS and the patients with DDD show that sCR1 is a potent inhibitor of C3 convertase activity, even in the presence of C3NeF.

EXAMPLE 2

Cfh−/− In Vivo Mouse Study

Complement factor H (CFH) deficiencies have been associated with dense deposit disease (DDD) and aHUS (Fakhouri et al., *Kidney International,* 78:279-286 (2010). Gene-targeted CFH-deficient mice (Cfh−/−) spontaneously develop low plasma C3 levels and deposition of C3 along the murine glomerular basement membrane, analogous to human dense deposit disease (Pickering, M C, et al., *Nat. Genet.,* 31:424-428 (2002)). Accordingly, Cfh−/− mice were selected as an animal model for this experiment.

Figure 3:
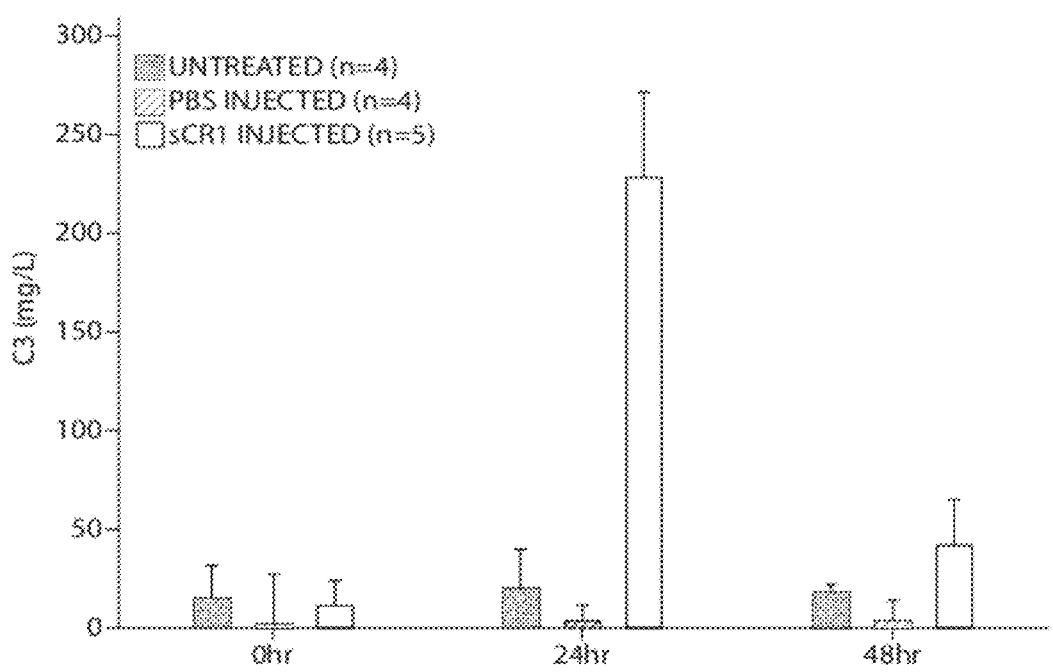
FIG. 3 is a graph showing the results of an in vivo study of C3 levels in Cfh−/− mice injected with a single dose of sCR1 at 50 mg/kg. C3 levels in sCR1-injected mice significantly increased after 24 hours.

Five Cfh−/− mice, a gift from Drs. Matthew Pickering and Marina Botto of the Imperial College London, were injected with sCR1 at a dose of 50 mg/kg (tail vein injection). As controls, one littermate was injected with the same amount of PBS and another one littermate was left untreated. Sera were collected by tail bleeding at 0, 24 and 48 hours. Serum C3 levels were measured using the mouse complement C3 kit (Kamiya Biomedical, Seattle, Wash.). C3 levels in sCR1-injected mice dramatically increased at 24 hours (rising close to the low end of normal reference values, ~300-1500 mg/L); however, C3 levels dropped to near pre-injection state by 48 hours in all injected mice (see, FIG. 3).

Kidneys were harvested at the time of euthanasia (48 hours) and imbedded in tissue-freezing medium (Triangle Biomedical Sciences, Durham, N.C.). Blocks were cut to a thickness of 5 micron and C3 deposition was assayed with FITC-conjugated C3 antibody (MP Biomedicals, Solon, Ohio).

Figure 4:
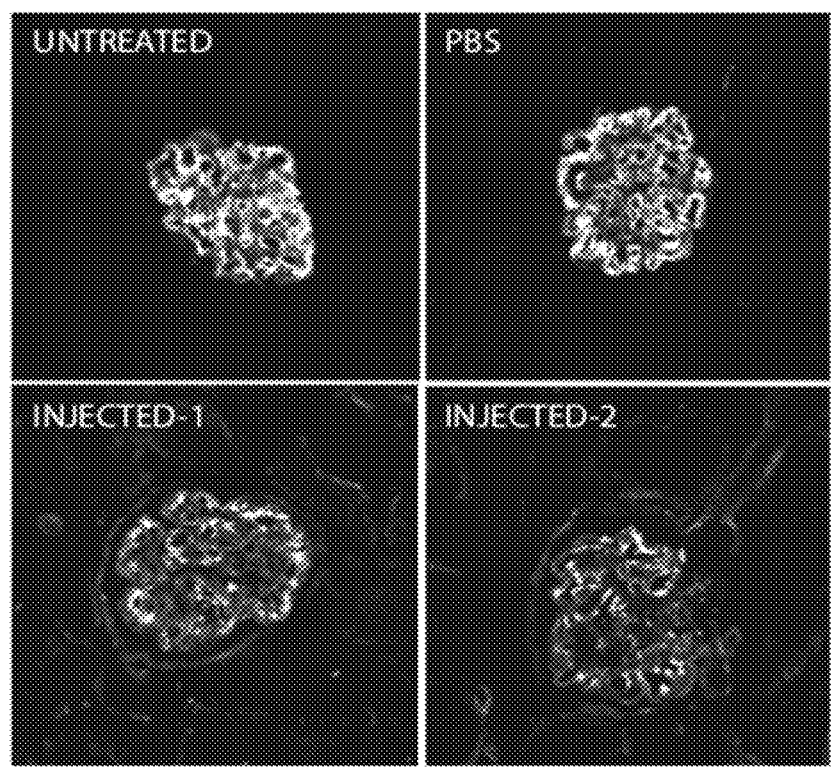
FIG. 4 are histopathologic slides comparing C3 deposition in the kidneys at 48 hours in a Cfh−/− test animal treated with a single does of sCR1 (Injected-1 and Injected-2) vs. the negative controls (Untreated and PBS).

C3 deposition was decreased in all sCR1-injected mice (see, FIG. 4). C3 immunofluorescence was decreased at 48 hours after a single dose of sCR1. By 48 hours, alternative pathway activation was again robust as evidenced by a decrease in C3 levels (see, FIG. 3). The decrease in C3 immunofluorescence reflects the transient control of C3 convertase activity over the 24 hour period following sCR1 injection.

Figure 5:
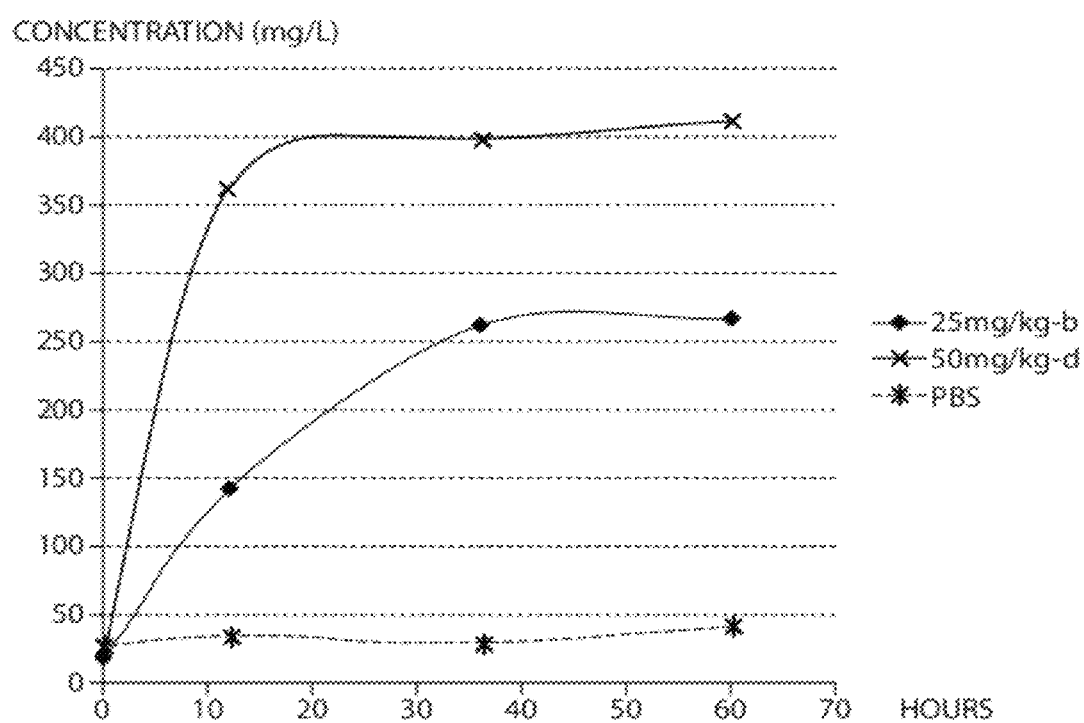
FIG. 5 is a graph showing the results of an in vivo study of C3 concentrations in Cfh−/−$_{tg\text{-}CR1}$ mice injected with 3 doses of sCR1 at 0, 24, and 48 hours at a dose of 25 mg/kg and 50 mg/kg. C3 concentration was measured at 0, 12, 36, and 60 hours.

The experiment was repeated, using Cfh−/−$_{tg-CR1}$ mice, a gift from Dr. Richard Quigg of the University of Chicago Medical Center (i.e., factor H-knock-out mice transgenic for human CR1). These mice are identical to the Cfh−/− mouse described above however they have been crossed with a mouse transgenic for human CR1 (Repik, A. et al., Clinical and Experimental Immunology, 140:230-240 (2005)). Four mice were injected (intraperitoneally) with sCR1 at 0, 24, and 48 hours (3 injections per mouse) at doses of either 25 mg/kg (2 mice) or 50 mg/kg (2 mice). As controls, two additional mice were injected with the same volume of PBS. C3 levels were measured at 0, 12, 36, and 60 hours. Because the Cfh−/−$_{tg-CR1}$ mouse expresses human CR1, it does not develop an immune response against sCR1 and is suitable for longer studies that employ multiple doses of sCR1. The results are shown in FIG. 5. C3 levels in sCR1-injected mice showed a dramatic and sustained increase (again, rising close to the low end of normal reference values, ~300-1500 mg/L).

Figure 6:
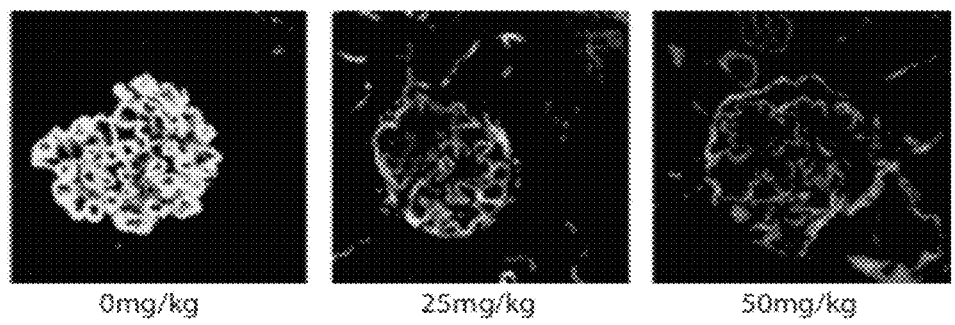
FIG. 6 are histopathologic slides comparing C3 deposition in the kidneys in Cfh−/−$_{tg\text{-}CR1}$ mouse test animals treated with a single dose of sCR1 (25 mg/kg and 50 mg/kg) vs. the negative control (0 mg/kg) at 60 hours post-injection.

Kidneys were harvested at the time of euthanasia (60 hours) and imbedded in tissue-freezing medium (Triangle Biomedical Sciences, Durham, N.C.). Blocks were cut to a thickness of 5 micron and C3 deposition was assayed with FITC-conjugated C3 antibody (MP Biomedicals, Solon, Ohio). The results are shown in FIG. 6.

C3 deposition was decreased in all sCR1-injected Cfh−/−$_{tg-CR1}$ mice at both concentrations (see, FIG. 5). C3 immunofluorescence was significantly decreased at 60 hours after the three-dose regimen sCR1 at 50 mg/kg. As seen in FIG. 6, the three-dose regimen, leading to sustained levels of sCR1 through the end of the experiment (see, FIG. 5), led to a remarkable decrease in C3 deposition on kidney sections at the end of the experiment. These results indicate that susceptible kidney tissues in DDD can be protected by systemic administration of sCR1.

These data indicate a treatment for the rare complement-mediated diseases of DDD (MPGN2) and/or aHUS and/or GN-C3 to alleviate undesired complement activity in the short term, and to improve or protect renal function in the long term.

Following the foregoing description, additional therapeutic formulations containing other embodiments of the complement regulatory protein sCR1 may readily be tested, prepared and used for the treatment of DDD (MPGN2) and/or aHUS and/or GN-C3. Additional embodiments of the invention and alternative methods adapted to a particular composition and mode of delivery will be evident from studying the foregoing description. All such embodiments and obvious alternatives are intended to be within the scope of this invention, as defined by the claims that follow.

Publications referred to above are hereby incorporated by reference.

A preferred soluble complement receptor type I polypeptide for use according to the present disclosure has the amino acid sequence:

(SEQ ID NO: 1)

```
Gln Cys Asn Ala Pro Glu Trp Leu Pro Phe Ala Arg Pro Thr Asn Leu
1               5                   10                  15
Thr Asp Glu Phe Glu Phe Pro Ile Gly Thr Tyr Leu Asn Tyr Glu Cys
                20                  25                  30
Arg Pro Gly Tyr Ser Gly Arg Pro Phe Ser Ile Ile Cys Leu Lys Asn
                35                  40                  45
Ser Val Trp Thr Gly Ala Lys Asp Arg Cys Arg Arg Lys Ser Cys Arg
    50                  55                  60
Asn Pro Pro Asp Pro Val Asn Gly Met Val His Val Ile Lys Gly Ile
65                  70                  75                  80
Gln Phe Gly Ser Gln Ile Lys Tyr Ser Cys Thr Lys Gly Tyr Arg Leu
                85                  90                  95
Ile Gly Ser Ser Ser Ala Thr Cys Ile Ile Ser Gly Asp Thr Val Ile
                100                 105                 110
Trp Asp Asn Glu Thr Pro Ile Cys Asp Arg Ile Pro Cys Gly Leu Pro
                115                 120                 125
Pro Thr Ile Thr Asn Gly Asp Phe Ile Ser Thr Asn Arg Glu Asn Phe
                130                 135                 140
His Tyr Gly Ser Val Val Thr Tyr Arg Cys Asn Pro Gly Ser Gly Gly
145                 150                 155                 160
Arg Lys Val Phe Glu Leu Val Gly Glu Pro Ser Ile Tyr Cys Thr Ser
                165                 170                 175
Asn Asp Asp Gln Val Gly Ile Trp Ser Gly Pro Ala Pro Gln Cys Ile
                180                 185                 190
Ile Pro Asn Lys Cys Thr Pro Pro Asn Val Glu Asn Gly Ile Leu Val
                195                 200                 205
Ser Asp Asn Arg Ser Leu Phe Ser Leu Asn Glu Val Val Glu Phe Arg
    210                 215                 220
Cys Gln Pro Gly Phe Val Met Lys Gly Pro Arg Arg Val Lys Cys Gln
225                 230                 235                 240
Ala Leu Asn Lys Trp Glu Pro Glu Leu Pro Ser Cys Ser Arg Val Cys
                245                 250                 255
Gln Pro Pro Pro Asp Val Leu His Ala Glu Arg Thr Gln Arg Asp Lys
                260                 265                 270
Asp Asn Phe Ser Pro Gly Gln Glu Val Phe Tyr Ser Cys Glu Pro Gly
        275                 280                 285
Tyr Asp Leu Arg Gly Ala Ala Ser Met Arg Cys Thr Pro Gln Gly Asp
    290                 295                 300
Trp Ser Pro Ala Ala Pro Thr Cys Glu Val Lys Ser Cys Asp Asp Phe
305                 310                 315                 320
Met Gly Gln Leu Leu Asn Gly Arg Val Leu Phe Pro Val Asn Leu Gln
                325                 330                 335
```

-continued

Leu Gly Ala Lys Val Asp Phe Val Cys Asp Glu Gly Phe Gln Leu Lys
            340                 345                 350

Gly Ser Ser Ala Ser Tyr Cys Val Leu Ala Gly Met Glu Ser Leu Trp
        355                 360                 365

Asn Ser Ser Val Pro Val Cys Glu Gln Ile Phe Cys Pro Ser Pro Pro
    370                 375                 380

Val Ile Pro Asn Gly Arg His Thr Gly Lys Pro Leu Glu Val Phe Pro
385                 390                 395                 400

Phe Gly Lys Ala Val Asn Tyr Thr Cys Asp Pro His Pro Asp Arg Gly
                405                 410                 415

Thr Ser Phe Asp Leu Ile Gly Glu Ser Thr Ile Arg Cys Thr Ser Asp
            420                 425                 430

Pro Gln Gly Asn Gly Val Trp Ser Ser Pro Ala Pro Arg Cys Gly Ile
        435                 440                 445

Leu Gly His Cys Gln Ala Pro Asp His Phe Leu Phe Ala Lys Leu Lys
    450                 455                 460

Thr Gln Thr Asn Ala Ser Asp Phe Pro Ile Gly Thr Ser Leu Lys Tyr
465                 470                 475                 480

Glu Cys Arg Pro Glu Tyr Tyr Gly Arg Pro Phe Ser Ile Thr Cys Leu
                485                 490                 495

Asp Asn Leu Val Trp Ser Ser Pro Lys Asp Val Cys Lys Arg Lys Ser
            500                 505                 510

Cys Lys Thr Pro Pro Asp Pro Val Asn Gly Met Val His Val Ile Thr
        515                 520                 525

Asp Ile Gln Val Gly Ser Arg Ile Asn Tyr Ser Cys Thr Thr Gly His
    530                 535                 540

Arg Leu Ile Gly His Ser Ser Ala Glu Cys Ile Leu Ser Gly Asn Ala
545                 550                 555                 560

Ala His Trp Ser Thr Lys Pro Pro Ile Cys Gln Arg Ile Pro Cys Gly
                565                 570                 575

Leu Pro Pro Thr Ile Ala Asn Gly Asp Phe Ile Ser Thr Asn Arg Glu
            580                 585                 590

Asn Phe His Tyr Gly Ser Val Val Thr Tyr Arg Cys Asn Pro Gly Ser
        595                 600                 605

Gly Gly Arg Lys Val Phe Glu Leu Val Gly Glu Pro Ser Ile Tyr Cys
    610                 615                 620

Thr Ser Asn Asp Asp Gln Val Gly Ile Trp Ser Gly Pro Ala Pro Gln
625                 630                 635                 640

Cys Ile Ile Pro Asn Lys Cys Thr Pro Pro Asn Val Glu Asn Gly Ile
                645                 650                 655

Leu Val Ser Asp Asn Arg Ser Leu Phe Ser Leu Asn Glu Val Val Glu
            660                 665                 670

Phe Arg Cys Gln Pro Gly Phe Val Met Lys Gly Pro Arg Arg Val Lys
        675                 680                 685

Cys Gln Ala Leu Asn Lys Trp Glu Pro Glu Leu Pro Ser Cys Ser Arg
    690                 695                 700

Val Cys Gln Pro Pro Pro Asp Val Leu His Ala Glu Arg Thr Gln Arg
705                 710                 715                 720

Asp Lys Asp Asn Phe Ser Pro Gly Gln Glu Val Phe Tyr Ser Cys Glu
                725                 730                 735

Pro Gly Tyr Asp Leu Arg Gly Ala Ala Ser Met Arg Cys Thr Pro Gln
            740                 745                 750

Gly Asp Trp Ser Pro Ala Ala Pro Thr Cys Glu Val Lys Ser Cys Asp
        755                 760                 765

-continued

```
Asp Phe Met Gly Gln Leu Leu Asn Gly Arg Val Phe Pro Val Asn
770                 775                 780
Leu Gln Leu Gly Ala Lys Val Asp Phe Val Cys Asp Glu Gly Phe Gln
785                 790                 795                 800
Leu Lys Gly Ser Ser Ala Ser Tyr Cys Val Leu Ala Gly Met Glu Ser
            805                 810                 815
Leu Trp Asn Ser Ser Val Pro Val Cys Glu Gln Ile Phe Cys Pro Ser
            820                 825                 830
Pro Pro Val Ile Pro Asn Gly Arg His Thr Gly Lys Pro Leu Glu Val
            835                 840                 845
Phe Pro Phe Gly Lys Ala Val Asn Tyr Thr Cys Asp Pro His Pro Asp
    850                 855                 860
Arg Gly Thr Ser Phe Asp Leu Ile Gly Glu Ser Thr Ile Arg Cys Thr
865                 870                 875                 880
Ser Asp Pro Gln Gly Asn Gly Val Trp Ser Ser Pro Ala Pro Arg Cys
                885                 890                 895
Gly Ile Leu Gly His Cys Gln Ala Pro Asp His Phe Leu Phe Ala Lys
            900                 905                 910
Leu Lys Thr Gln Thr Asn Ala Ser Asp Phe Pro Ile Gly Thr Ser Leu
    915                 920                 925
Lys Tyr Glu Cys Arg Pro Glu Tyr Tyr Gly Arg Pro Phe Ser Ile Thr
930                 935                 940
Cys Leu Asp Asn Leu Val Trp Ser Ser Pro Lys Asp Val Cys Lys Arg
945                 950                 955                 960
Lys Ser Cys Lys Thr Pro Pro Asp Pro Val Asn Gly Met Val His Val
                965                 970                 975
Ile Thr Asp Ile Gln Val Gly Ser Arg Ile Asn Tyr Ser Cys Thr Thr
            980                 985                 990
Gly His Arg Leu Ile Gly His Ser Ser Ala Glu Cys Ile Leu Ser Gly
    995                 1000                1005
Asn Thr Ala His Trp Ser Thr Lys Pro Pro Ile Cys Gln Arg Ile
    1010                1015                1020
Pro Cys Gly Leu Pro Pro Thr Ile Ala Asn Gly Asp Phe Ile Ser
    1025                1030                1035
Thr Asn Arg Glu Asn Phe His Tyr Gly Ser Val Val Thr Tyr Arg
    1040                1045                1050
Cys Asn Leu Gly Ser Arg Gly Arg Lys Val Phe Glu Leu Val Gly
    1055                1060                1065
Glu Pro Ser Ile Tyr Cys Thr Ser Asn Asp Asp Gln Val Gly Ile
    1070                1075                1080
Trp Ser Gly Pro Ala Pro Gln Cys Ile Ile Pro Asn Lys Cys Thr
    1085                1090                1095
Pro Pro Asn Val Glu Asn Gly Ile Leu Val Ser Asp Asn Arg Ser
    1100                1105                1110
Leu Phe Ser Leu Asn Glu Val Val Glu Phe Arg Cys Gln Pro Gly
    1115                1120                1125
Phe Val Met Lys Gly Pro Arg Arg Val Lys Cys Gln Ala Leu Asn
    1130                1135                1140
Lys Trp Glu Pro Glu Leu Pro Ser Cys Ser Arg Val Cys Gln Pro
    1145                1150                1155
Pro Pro Glu Ile Leu His Gly Glu His Thr Pro Ser His Gln Asp
    1160                1165                1170
Asn Phe Ser Pro Gly Gln Glu Val Phe Tyr Ser Cys Glu Pro Gly
    1175                1180                1185
```

```
Tyr Asp Leu Arg Gly Ala Ala Ser Leu His Cys Thr Pro Gln Gly
    1190                1195                1200

Asp Trp Ser Pro Glu Ala Pro Arg Cys Ala Val Lys Ser Cys Asp
    1205                1210                1215

Asp Phe Leu Gly Gln Leu Pro His Gly Arg Val Leu Phe Pro Leu
    1220                1225                1230

Asn Leu Gln Leu Gly Ala Lys Val Ser Phe Val Cys Asp Glu Gly
    1235                1240                1245

Phe Arg Leu Lys Gly Ser Ser Val Ser His Cys Val Leu Val Gly
    1250                1255                1260

Met Arg Ser Leu Trp Asn Asn Ser Val Pro Val Cys Glu His Ile
    1265                1270                1275

Phe Cys Pro Asn Pro Pro Ala Ile Leu Asn Gly Arg His Thr Gly
    1280                1285                1290

Thr Pro Ser Gly Asp Ile Pro Tyr Gly Lys Glu Ile Ser Tyr Thr
    1295                1300                1305

Cys Asp Pro His Pro Asp Arg Gly Met Thr Phe Asn Leu Ile Gly
    1310                1315                1320

Glu Ser Thr Ile Arg Cys Thr Ser Asp Pro His Gly Asn Gly Val
    1325                1330                1335

Trp Ser Ser Pro Ala Pro Arg Cys Glu Leu Ser Val Arg Ala Gly
    1340                1345                1350

His Cys Lys Thr Pro Glu Gln Phe Pro Phe Ala Ser Pro Thr Ile
    1355                1360                1365

Pro Ile Asn Asp Phe Glu Phe Pro Val Gly Thr Ser Leu Asn Tyr
    1370                1375                1380

Glu Cys Arg Pro Gly Tyr Phe Gly Lys Met Phe Ser Ile Ser Cys
    1385                1390                1395

Leu Glu Asn Leu Val Trp Ser Ser Val Glu Asp Asn Cys Arg Arg
    1400                1405                1410

Lys Ser Cys Gly Pro Pro Pro Glu Pro Phe Asn Gly Met Val His
    1415                1420                1425

Ile Asn Thr Asp Thr Gln Phe Gly Ser Thr Val Asn Tyr Ser Cys
    1430                1435                1440

Asn Glu Gly Phe Arg Leu Ile Gly Ser Pro Ser Thr Thr Cys Leu
    1445                1450                1455

Val Ser Gly Asn Asn Val Thr Trp Asp Lys Lys Ala Pro Ile Cys
    1460                1465                1470

Glu Ile Ile Ser Cys Glu Pro Pro Pro Thr Ile Ser Asn Gly Asp
    1475                1480                1485

Phe Tyr Ser Asn Asn Arg Thr Ser Phe His Asn Gly Thr Val Val
    1490                1495                1500

Thr Tyr Gln Cys His Thr Gly Pro Asp Gly Glu Gln Leu Phe Glu
    1505                1510                1515

Leu Val Gly Glu Arg Ser Ile Tyr Cys Thr Ser Lys Asp Asp Gln
    1520                1525                1530

Val Gly Val Trp Ser Ser Pro Pro Pro Arg Cys Ile Ser Thr Asn
    1535                1540                1545

Lys Cys Thr Ala Pro Glu Val Glu Asn Ala Ile Arg Val Pro Gly
    1550                1555                1560

Asn Arg Ser Phe Phe Ser Leu Thr Glu Ile Ile Arg Phe Arg Cys
    1565                1570                1575

Gln Pro Gly Phe Val Met Val Gly Ser His Thr Val Gln Cys Gln
    1580                1585                1590
```

-continued

```
Thr Asn Gly Arg Trp Gly Pro Lys Leu Pro His Cys Ser Arg Val
    1595                1600                1605

Cys Gln Pro Pro Glu Ile Leu His Gly Glu His Thr Leu Ser
    1610                1615                1620

His Gln Asp Asn Phe Ser Pro Gly Gln Glu Val Phe Tyr Ser Cys
    1625                1630                1635

Glu Pro Ser Tyr Asp Leu Arg Gly Ala Ala Ser Leu His Cys Thr
    1640                1645                1650

Pro Gln Gly Asp Trp Ser Pro Glu Ala Pro Arg Cys Thr Val Lys
    1655                1660                1665

Ser Cys Asp Asp Phe Leu Gly Gln Leu Pro His Gly Arg Val Leu
    1670                1675                1680

Leu Pro Leu Asn Leu Gln Leu Gly Ala Lys Val Ser Phe Val Cys
    1685                1690                1695

Asp Glu Gly Phe Arg Leu Lys Gly Arg Ser Ala Ser His Cys Val
    1700                1705                1710

Leu Ala Gly Met Lys Ala Leu Trp Asn Ser Ser Val Pro Val Cys
    1715                1720                1725

Glu Gln Ile Phe Cys Pro Asn Pro Pro Ala Ile Leu Asn Gly Arg
    1730                1735                1740

His Thr Gly Thr Pro Phe Gly Asp Ile Pro Tyr Gly Lys Glu Ile
    1745                1750                1755

Ser Tyr Ala Cys Asp Thr His Pro Asp Arg Gly Met Thr Phe Asn
    1760                1765                1770

Leu Ile Gly Glu Ser Ser Ile Arg Cys Thr Ser Asp Pro Gln Gly
    1775                1780                1785

Asn Gly Val Trp Ser Ser Pro Ala Pro Arg Cys Glu Leu Ser Val
    1790                1795                1800

Pro Ala Ala Cys Pro His Pro Pro Lys Ile Gln Asn Gly His Tyr
    1805                1810                1815

Ile Gly Gly His Val Ser Leu Tyr Leu Pro Gly Met Thr Ile Ser
    1820                1825                1830

Tyr Ile Cys Asp Pro Gly Tyr Leu Leu Val Gly Lys Gly Phe Ile
    1835                1840                1845

Phe Cys Thr Asp Gln Gly Ile Trp Ser Gln Leu Asp His Tyr Cys
    1850                1855                1860

Lys Glu Val Asn Cys Ser Phe Pro Leu Phe Met Asn Gly Ile Ser
    1865                1870                1875

Lys Glu Leu Glu Met Lys Lys Val Tyr His Tyr Gly Asp Tyr Val
    1880                1885                1890

Thr Leu Lys Cys Glu Asp Gly Tyr Thr Leu Glu Gly Ser Pro Trp
    1895                1900                1905

Ser Gln Cys Gln Ala Asp Asp Arg Trp Asp Pro Pro Leu Ala Lys
    1910                1915                1920

Cys Thr Ser Arg Ala His Asp Ala
    1925                1930
```

---

What is claimed is:

1. A method for treating dense deposit disease (DDD) and/or glomerulonephritis with isolated C3 deposits (GN-C3) in a mammalian subject comprising administering to a mammalian subject in need of treatment an effective amount of a soluble complement receptor type I (sCR1) polypeptide.

2. The method according to claim 1, wherein said soluble CR1 polypeptide is selected from the group consisting of:
   a fragment of human CR1 comprising at least short consensus repeats 8-11;
   a fragment of human CR1 comprising at least short consensus repeats 15-18;
   a soluble CR1 polypeptide comprising human CR1 short consensus repeats 8-11 and 15-18;
   a fragment of human CR1 comprising long homologous repeat B;
   a fragment of human CR1 comprising long homologous repeat C;
   a fragment of human CR1 comprising long homologous repeats B and C;

a fragment of human CR1 comprising long homologous repeats B, C and D;
a fragment of human CR1 comprising at least long homologous repeats A and B;
a fragment of human CR1 comprising long homologous repeats A, B and C;
a fragment of human CR1 comprising long homologous repeats A, B, C and D;
a fragment of human CR1 comprising the extracellular domain of CR1;
a fragment of human CR1 comprising the extracellular domain of CR1 and having the N-terminal LHR A deleted (sCR1[desLHR-A]);
a soluble CR1 polypeptide having modified glycosylation to improve serum half-life in vivo;
a soluble CR1 polypeptide having glycosylation modified to exhibit sialyl Lewis X moieties (sCR1-sLe$^x$);
a soluble CR1 construct having two or more CR1 polypeptide moieties linked to a carrier molecule; and
combinations thereof.

3. The method according to claim 2, wherein said soluble CR1 polypeptide is selected from the group consisting of:
a fragment of human CR1 comprising the extracellular domain of CR1;
a soluble CR1 polypeptide having modified glycosylation to improve serum half-life in vivo;
a soluble CR1 polypeptide having glycosylation modified to exhibit sialyl Lewis X moieties (sCR1-sLe$^x$); and
combinations thereof.

4. The method accordingly to claim 2, wherein said soluble CR1 polypeptide exhibits a complement regulatory activity selected from the group consisting of:
(i) the ability to bind C3b;
(ii) the ability to bind C4b;
(iii) the abilities to bind C3b and to bind C4b;
(iv) factor I cofactor activity;
(v) the ability to inhibit classical C3 convertase activity;
(vi) the ability to inhibit alternative C3 convertase activity;
(vii) the ability to inhibit classical C5 convertase activity;
(viii) the ability to inhibit alternative C5 convertase activity;
(ix) the ability to inhibit neutrophil oxidative burst;
(x) the ability to inhibit complement-mediated hemolysis;
(xi) the ability to inhibit C3a production; and
(xii) the ability to inhibit C5a production.

5. The method according to claim 1, wherein said soluble CR1 polypeptide exhibits the ability to inhibit complement activation via both the classical activation pathway and the alternative activation pathway.

6. The method according to claim 4, wherein said mammalian subject is a human.

7. The method according to claim 6, wherein the administration of said soluble CR1 polypeptide reduces further C3 deposition in kidney tissue.

8. The method according to claim 6, wherein the administration of said soluble CR1 polypeptide at least partially reverses existing C3 deposition in kidney tissue.

9. The method according to claim 6, wherein the administration of said soluble CR1 polypeptide reduces kidney damage.

10. The method according to claim 9, wherein the administration of said soluble CR1 polypeptide reduces further kidney damage.

11. The method according to claim 9 wherein the administration of said soluble CR1 polypeptide at least partially reverses existing kidney damage.

12. The method according to claim 6, wherein the administration of said soluble CR1 polypeptide reduces deterioration in renal function.

13. The method according to claim 6, wherein the administration of said soluble CR1 polypeptide improves renal function.

14. The method according to claim 13, wherein the administration of said soluble CR1 polypeptide improves renal function as indicated by one or more of i) reduced proteinuria, ii) reduced serum creatinine, and/or iii) improved glomerular filtration rate.

15. The method according to claim 6, wherein the administration of said soluble CR1 polypeptide increases serum levels of C3.

16. The method according to claim 6, wherein said human subject suffers from dense deposit disease (DDD).

17. The method according to claim 6, wherein said human subject suffers from primary glomerulonephritis with isolated C3 deposits (GN-C3).

18. The method according to according to claim 1, wherein said polypeptide is administered by an intradermal, intramuscular, intraperitoneal, intravenous, subcutaneous, intrathecal, epidural, oral or pulmonary route.

19. A method for treating dense deposit disease (DDD) and/or glomerulonephritis with isolated C3 deposits (GN-C3) in a mammalian subject comprising administering to a mammalian subject in need of treatment an effective amount of a soluble complement receptor type I (sCR1) polypeptide comprising the extracellular domain of mature human CR1 (SEQ ID NO: 1).

* * * * *

SEQUENCE LISTING

<160> NUMBER OF SEQ ID NOS: 1

<210> SEQ ID NO 1
<211> LENGTH: 1931
<212> TYPE: PRT
<213> ORGANISM: Homo sapiens

```
<220> FEATURE:
<221> NAME/KEY: MISC_FEATURE
<222> LOCATION: (1)..(1931)
<223> OTHER INFORMATION: soluble CR1 polypeptide

<400> SEQUENCE: 1

Gln Cys Asn Ala Pro Glu Trp Leu Pro Phe Ala Arg Pro Thr Asn Leu
1               5                   10                  15

Thr Asp Glu Phe Glu Phe Pro Ile Gly Thr Tyr Leu Asn Tyr Glu Cys
            20                  25                  30

Arg Pro Gly Tyr Ser Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Gly Ile
65                  70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asp Thr Val Ile
            100                 105                 110

Trp Asp Asn Glu Thr Pro Ile Cys Asp Arg Ile Pro Cys Gly Leu Pro
        115                 120                 125

Pro Thr Ile Thr Asn Gly Asp Phe Ile Ser Thr Asn Arg Glu Asn Phe
    130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

Ile Pro Asn Lys Cys Thr Pro Pro Asn Val Glu Asn Gly Ile Leu Val
        195                 200                 205

Ser Asp Asn Arg Ser Leu Phe Ser Leu Asn Glu Val Val Glu Phe Arg
    210                 215                 220

Cys Gln Pro Gly Phe Val Met Lys Gly Pro Arg Arg Val Lys Cys Gln
225                 230                 235                 240

Ala Leu Asn Lys Trp Glu Pro Glu Leu Pro Ser Cys Ser Arg Val Cys
                245                 250                 255

Gln Pro Pro Pro Asp Val Leu His Ala Glu Arg Thr Gln Arg Asp Lys
            260                 265                 270

Asp Asn Phe Ser Pro Gly Gln Glu Val Phe Tyr Ser Cys Glu Pro Gly
        275                 280                 285

Tyr Asp Leu Arg Gly Ala Ala Ser Met Arg Cys Thr Pro Gln Gly Asp
    290                 295                 300

Trp Ser Pro Ala Ala Pro Thr Cys Glu Val Lys Ser Cys Asp Asp Phe
305                 310                 315                 320

Met Gly Gln Leu Leu Asn Gly Arg Val Leu Phe Pro Val Asn Leu Gln
                325                 330                 335

Leu Gly Ala Lys Val Asp Phe Val Cys Asp Glu Gly Phe Gln Leu Lys
            340                 345                 350

Gly Ser Ser Ala Ser Tyr Cys Val Leu Ala Gly Met Glu Ser Leu Trp
        355                 360                 365

Asn Ser Ser Val Pro Val Cys Glu Gln Ile Phe Cys Pro Ser Pro Pro
    370                 375                 380
```

-continued

Val Ile Pro Asn Gly Arg His Thr Gly Lys Pro Leu Glu Val Phe Pro
385                 390                 395                 400

Phe Gly Lys Ala Val Asn Tyr Thr Cys Asp Pro His Pro Asp Arg Gly
            405                 410                 415

Thr Ser Phe Asp Leu Ile Gly Glu Ser Thr Ile Arg Cys Thr Ser Asp
        420                 425                 430

Pro Gln Gly Asn Gly Val Trp Ser Ser Pro Ala Pro Arg Cys Gly Ile
    435                 440                 445

Leu Gly His Cys Gln Ala Pro Asp His Phe Leu Phe Ala Lys Leu Lys
450                 455                 460

Thr Gln Thr Asn Ala Ser Asp Phe Pro Ile Gly Thr Ser Leu Lys Tyr
465                 470                 475                 480

Glu Cys Arg Pro Glu Tyr Tyr Gly Arg Pro Phe Ser Ile Thr Cys Leu
            485                 490                 495

Asp Asn Leu Val Trp Ser Ser Pro Lys Asp Val Cys Lys Arg Lys Ser
        500                 505                 510

Cys Lys Thr Pro Pro Asp Pro Val Asn Gly Met Val His Val Ile Thr
    515                 520                 525

Asp Ile Gln Val Gly Ser Arg Ile Asn Tyr Ser Cys Thr Thr Gly His
530                 535                 540

Arg Leu Ile Gly His Ser Ser Ala Glu Cys Ile Leu Ser Gly Asn Ala
545                 550                 555                 560

Ala His Trp Ser Thr Lys Pro Pro Ile Cys Gln Arg Ile Pro Cys Gly
            565                 570                 575

Leu Pro Pro Thr Ile Ala Asn Gly Asp Phe Ile Ser Thr Asn Arg Glu
        580                 585                 590

Asn Phe His Tyr Gly Ser Val Val Thr Tyr Arg Cys Asn Pro Gly Ser
    595                 600                 605

Gly Gly Arg Lys Val Phe Glu Leu Val Gly Glu Pro Ser Ile Tyr Cys
610                 615                 620

Thr Ser Asn Asp Asp Gln Val Gly Ile Trp Ser Gly Pro Ala Pro Gln
625                 630                 635                 640

Cys Ile Ile Pro Asn Lys Cys Thr Pro Pro Asn Val Glu Asn Gly Ile
            645                 650                 655

Leu Val Ser Asp Asn Arg Ser Leu Phe Ser Leu Asn Glu Val Val Glu
        660                 665                 670

Phe Arg Cys Gln Pro Gly Phe Val Met Lys Gly Pro Arg Arg Val Lys
    675                 680                 685

Cys Gln Ala Leu Asn Lys Trp Glu Pro Glu Leu Pro Ser Cys Ser Arg
690                 695                 700

Val Cys Gln Pro Pro Pro Asp Val Leu His Ala Glu Arg Thr Gln Arg
705                 710                 715                 720

Asp Lys Asp Asn Phe Ser Pro Gly Gln Glu Val Phe Tyr Ser Cys Glu
            725                 730                 735

Pro Gly Tyr Asp Leu Arg Gly Ala Ala Ser Met Arg Cys Thr Pro Gln
        740                 745                 750

Gly Asp Trp Ser Pro Ala Ala Pro Thr Cys Glu Val Lys Ser Cys Asp
    755                 760                 765

Asp Phe Met Gly Gln Leu Leu Asn Gly Arg Val Leu Phe Pro Val Asn
770                 775                 780

Leu Gln Leu Gly Ala Lys Val Asp Phe Val Cys Asp Glu Gly Phe Gln
785                 790                 795                 800

Leu Lys Gly Ser Ser Ala Ser Tyr Cys Val Leu Ala Gly Met Glu Ser

```
                805                 810                 815
Leu Trp Asn Ser Ser Val Pro Val Cys Glu Gln Ile Phe Cys Pro Ser
            820                 825                 830

Pro Pro Val Ile Pro Asn Gly Arg His Thr Gly Lys Pro Leu Glu Val
        835                 840                 845

Phe Pro Phe Gly Lys Ala Val Asn Tyr Thr Cys Asp Pro His Pro Asp
    850                 855                 860

Arg Gly Thr Ser Phe Asp Leu Ile Gly Glu Ser Thr Ile Arg Cys Thr
865                 870                 875                 880

Ser Asp Pro Gln Gly Asn Gly Val Trp Ser Ser Pro Ala Pro Arg Cys
                885                 890                 895

Gly Ile Leu Gly His Cys Gln Ala Pro Asp His Phe Leu Phe Ala Lys
            900                 905                 910

Leu Lys Thr Gln Thr Asn Ala Ser Asp Phe Pro Ile Gly Thr Ser Leu
        915                 920                 925

Lys Tyr Glu Cys Arg Pro Glu Tyr Tyr Gly Arg Pro Phe Ser Ile Thr
    930                 935                 940

Cys Leu Asp Asn Leu Val Trp Ser Ser Pro Lys Asp Val Cys Lys Arg
945                 950                 955                 960

Lys Ser Cys Lys Thr Pro Pro Asp Pro Val Asn Gly Met Val His Val
                965                 970                 975

Ile Thr Asp Ile Gln Val Gly Ser Arg Ile Asn Tyr Ser Cys Thr Thr
            980                 985                 990

Gly His Arg Leu Ile Gly His Ser Ser Ala Glu Cys Ile Leu Ser Gly
            995                 1000                1005

Asn Thr Ala His Trp Ser Thr Lys Pro Pro Ile Cys Gln Arg Ile
    1010                1015                1020

Pro Cys Gly Leu Pro Pro Thr Ile Ala Asn Gly Asp Phe Ile Ser
    1025                1030                1035

Thr Asn Arg Glu Asn Phe His Tyr Gly Ser Val Val Thr Tyr Arg
    1040                1045                1050

Cys Asn Leu Gly Ser Arg Gly Arg Lys Val Phe Glu Leu Val Gly
    1055                1060                1065

Glu Pro Ser Ile Tyr Cys Thr Ser Asn Asp Asp Gln Val Gly Ile
    1070                1075                1080

Trp Ser Gly Pro Ala Pro Gln Cys Ile Ile Pro Asn Lys Cys Thr
    1085                1090                1095

Pro Pro Asn Val Glu Asn Gly Ile Leu Val Ser Asp Asn Arg Ser
    1100                1105                1110

Leu Phe Ser Leu Asn Glu Val Val Glu Phe Arg Cys Gln Pro Gly
    1115                1120                1125

Phe Val Met Lys Gly Pro Arg Arg Val Lys Cys Gln Ala Leu Asn
    1130                1135                1140

Lys Trp Glu Pro Glu Leu Pro Ser Cys Ser Arg Val Cys Gln Pro
    1145                1150                1155

Pro Pro Glu Ile Leu His Gly Glu His Thr Pro Ser His Gln Asp
    1160                1165                1170

Asn Phe Ser Pro Gly Gln Glu Val Phe Tyr Ser Cys Glu Pro Gly
    1175                1180                1185

Tyr Asp Leu Arg Gly Ala Ala Ser Leu His Cys Thr Pro Gln Gly
    1190                1195                1200

Asp Trp Ser Pro Glu Ala Pro Arg Cys Ala Val Lys Ser Cys Asp
    1205                1210                1215
```

-continued

```
Asp Phe Leu Gly Gln Leu Pro His Gly Arg Val Leu Phe Pro Leu
    1220                1225                1230

Asn Leu Gln Leu Gly Ala Lys Val Ser Phe Val Cys Asp Glu Gly
    1235                1240                1245

Phe Arg Leu Lys Gly Ser Ser Val Ser His Cys Val Leu Val Gly
    1250                1255                1260

Met Arg Ser Leu Trp Asn Asn Ser Val Pro Val Cys Glu His Ile
    1265                1270                1275

Phe Cys Pro Asn Pro Pro Ala Ile Leu Asn Gly Arg His Thr Gly
    1280                1285                1290

Thr Pro Ser Gly Asp Ile Pro Tyr Gly Lys Glu Ile Ser Tyr Thr
    1295                1300                1305

Cys Asp Pro His Pro Asp Arg Gly Met Thr Phe Asn Leu Ile Gly
    1310                1315                1320

Glu Ser Thr Ile Arg Cys Thr Ser Asp Pro His Gly Asn Gly Val
    1325                1330                1335

Trp Ser Ser Pro Ala Pro Arg Cys Glu Leu Ser Val Arg Ala Gly
    1340                1345                1350

His Cys Lys Thr Pro Glu Gln Phe Pro Phe Ala Ser Pro Thr Ile
    1355                1360                1365

Pro Ile Asn Asp Phe Glu Phe Pro Val Gly Thr Ser Leu Asn Tyr
    1370                1375                1380

Glu Cys Arg Pro Gly Tyr Phe Gly Lys Met Phe Ser Ile Ser Cys
    1385                1390                1395

Leu Glu Asn Leu Val Trp Ser Ser Val Glu Asp Asn Cys Arg Arg
    1400                1405                1410

Lys Ser Cys Gly Pro Pro Pro Glu Pro Phe Asn Gly Met Val His
    1415                1420                1425

Ile Asn Thr Asp Thr Gln Phe Gly Ser Thr Val Asn Tyr Ser Cys
    1430                1435                1440

Asn Glu Gly Phe Arg Leu Ile Gly Ser Pro Ser Thr Thr Cys Leu
    1445                1450                1455

Val Ser Gly Asn Asn Val Thr Trp Asp Lys Lys Ala Pro Ile Cys
    1460                1465                1470

Glu Ile Ile Ser Cys Glu Pro Pro Pro Thr Ile Ser Asn Gly Asp
    1475                1480                1485

Phe Tyr Ser Asn Asn Arg Thr Ser Phe His Asn Gly Thr Val Val
    1490                1495                1500

Thr Tyr Gln Cys His Thr Gly Pro Asp Gly Glu Gln Leu Phe Glu
    1505                1510                1515

Leu Val Gly Glu Arg Ser Ile Tyr Cys Thr Ser Lys Asp Asp Gln
    1520                1525                1530

Val Gly Val Trp Ser Ser Pro Pro Pro Arg Cys Ile Ser Thr Asn
    1535                1540                1545

Lys Cys Thr Ala Pro Glu Val Glu Asn Ala Ile Arg Val Pro Gly
    1550                1555                1560

Asn Arg Ser Phe Phe Ser Leu Thr Glu Ile Ile Arg Phe Arg Cys
    1565                1570                1575

Gln Pro Gly Phe Val Met Val Gly Ser His Thr Val Gln Cys Gln
    1580                1585                1590

Thr Asn Gly Arg Trp Gly Pro Lys Leu Pro His Cys Ser Arg Val
    1595                1600                1605
```

| | | | | | | | | | | | |
|---|---|---|---|---|---|---|---|---|---|---|---|
| Cys | Gln | Pro | Pro | Pro | Glu | Ile | Leu | His | Gly | Glu | His | Thr | Leu | Ser |
| | 1610 | | | | | 1615 | | | | | 1620 | | | |
| His | Gln | Asp | Asn | Phe | Ser | Pro | Gly | Gln | Glu | Val | Phe | Tyr | Ser | Cys |
| | 1625 | | | | | 1630 | | | | | 1635 | | | |
| Glu | Pro | Ser | Tyr | Asp | Leu | Arg | Gly | Ala | Ala | Ser | Leu | His | Cys | Thr |
| | 1640 | | | | | 1645 | | | | | 1650 | | | |
| Pro | Gln | Gly | Asp | Trp | Ser | Pro | Glu | Ala | Pro | Arg | Cys | Thr | Val | Lys |
| | 1655 | | | | | 1660 | | | | | 1665 | | | |
| Ser | Cys | Asp | Asp | Phe | Leu | Gly | Gln | Leu | Pro | His | Gly | Arg | Val | Leu |
| | 1670 | | | | | 1675 | | | | | 1680 | | | |
| Leu | Pro | Leu | Asn | Leu | Gln | Leu | Gly | Ala | Lys | Val | Ser | Phe | Val | Cys |
| | 1685 | | | | | 1690 | | | | | 1695 | | | |
| Asp | Glu | Gly | Phe | Arg | Leu | Lys | Gly | Arg | Ser | Ala | Ser | His | Cys | Val |
| | 1700 | | | | | 1705 | | | | | 1710 | | | |
| Leu | Ala | Gly | Met | Lys | Ala | Leu | Trp | Asn | Ser | Ser | Val | Pro | Val | Cys |
| | 1715 | | | | | 1720 | | | | | 1725 | | | |
| Glu | Gln | Ile | Phe | Cys | Pro | Asn | Pro | Pro | Ala | Ile | Leu | Asn | Gly | Arg |
| | 1730 | | | | | 1735 | | | | | 1740 | | | |
| His | Thr | Gly | Thr | Pro | Phe | Gly | Asp | Ile | Pro | Tyr | Gly | Lys | Glu | Ile |
| | 1745 | | | | | 1750 | | | | | 1755 | | | |
| Ser | Tyr | Ala | Cys | Asp | Thr | His | Pro | Asp | Arg | Gly | Met | Thr | Phe | Asn |
| | 1760 | | | | | 1765 | | | | | 1770 | | | |
| Leu | Ile | Gly | Glu | Ser | Ser | Ile | Arg | Cys | Thr | Ser | Asp | Pro | Gln | Gly |
| | 1775 | | | | | 1780 | | | | | 1785 | | | |
| Asn | Gly | Val | Trp | Ser | Ser | Pro | Ala | Pro | Arg | Cys | Glu | Leu | Ser | Val |
| | 1790 | | | | | 1795 | | | | | 1800 | | | |
| Pro | Ala | Ala | Cys | Pro | His | Pro | Pro | Lys | Ile | Gln | Asn | Gly | His | Tyr |
| | 1805 | | | | | 1810 | | | | | 1815 | | | |
| Ile | Gly | Gly | His | Val | Ser | Leu | Tyr | Leu | Pro | Gly | Met | Thr | Ile | Ser |
| | 1820 | | | | | 1825 | | | | | 1830 | | | |
| Tyr | Ile | Cys | Asp | Pro | Gly | Tyr | Leu | Leu | Val | Gly | Lys | Gly | Phe | Ile |
| | 1835 | | | | | 1840 | | | | | 1845 | | | |
| Phe | Cys | Thr | Asp | Gln | Gly | Ile | Trp | Ser | Gln | Leu | Asp | His | Tyr | Cys |
| | 1850 | | | | | 1855 | | | | | 1860 | | | |
| Lys | Glu | Val | Asn | Cys | Ser | Phe | Pro | Leu | Phe | Met | Asn | Gly | Ile | Ser |
| | 1865 | | | | | 1870 | | | | | 1875 | | | |
| Lys | Glu | Leu | Glu | Met | Lys | Lys | Val | Tyr | His | Tyr | Gly | Asp | Tyr | Val |
| | 1880 | | | | | 1885 | | | | | 1890 | | | |
| Thr | Leu | Lys | Cys | Glu | Asp | Gly | Tyr | Thr | Leu | Glu | Gly | Ser | Pro | Trp |
| | 1895 | | | | | 1900 | | | | | 1905 | | | |
| Ser | Gln | Cys | Gln | Ala | Asp | Asp | Arg | Trp | Asp | Pro | Pro | Leu | Ala | Lys |
| | 1910 | | | | | 1915 | | | | | 1920 | | | |
| Cys | Thr | Ser | Arg | Ala | His | Asp | Ala |
| | 1925 | | | | | 1930 | |